(12) United States Patent
Bannen et al.

(10) Patent No.: US 10,427,126 B2
(45) Date of Patent: Oct. 1, 2019

(54) SYSTEM AND METHOD FOR LONGITUDINAL ANALYSIS OF PEPTIDE SYNTHESIS

(71) Applicant: Roche Sequencing Solutions, Inc., Pleasanton, CA (US)

(72) Inventors: Ryan Bannen, Madison, WI (US); Sarah Barilovits, Madison, WI (US); Jigar Patel, Verona, WI (US); Eric Sullivan, Madison, WI (US); John Tan, Madison, WI (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 270 days.

(21) Appl. No.: 15/259,893

(22) Filed: Sep. 8, 2016

(65) Prior Publication Data

US 2017/0120212 A1 May 4, 2017

Related U.S. Application Data

(60) Provisional application No. 62/247,485, filed on Oct. 28, 2015.

(51) Int. Cl.
| | |
|---|---|
| *B01J 19/00* | (2006.01) |
| *G01N 33/68* | (2006.01) |
| *C07K 1/04* | (2006.01) |
| *C07K 17/14* | (2006.01) |
| *G01N 21/64* | (2006.01) |
| *C40B 50/16* | (2006.01) |

(52) U.S. Cl.
CPC ......... *B01J 19/0046* (2013.01); *C07K 1/047* (2013.01); *C07K 17/14* (2013.01); *G01N 21/6452* (2013.01); *G01N 33/6845* (2013.01); *B01J 2219/00585* (2013.01); *B01J 2219/00596* (2013.01); *B01J 2219/00623* (2013.01); *B01J 2219/00659* (2013.01); *B01J 2219/00693* (2013.01); *B01J 2219/00695* (2013.01); *B01J 2219/00725* (2013.01); *C40B 50/16* (2013.01)

(58) Field of Classification Search
None
See application file for complete search history.

(56) References Cited

U.S. PATENT DOCUMENTS

| | | |
|---|---|---|
| 2002/0137096 A1 | 9/2002 | Fodor et al. |
| 2015/0185216 A1* | 7/2015 | Albert et al. ........ G01N 33/573 506/1 |

FOREIGN PATENT DOCUMENTS

| | | | | |
|---|---|---|---|---|
| EP | 0955085 A2 | 11/1999 | | |
| WO | 2004003233 A1 | 1/2004 | | |
| WO | WO-2004003233 A1 * | 1/2004 | ............. | B82Y 30/00 |
| WO | 2014144383 A1 | 9/2014 | | |
| WO | 2014145123 A2 | 9/2014 | | |
| WO | WO-2014145123 A2 * | 9/2014 | ......... | G01N 33/6845 |

\* cited by examiner

*Primary Examiner* — Kaijiang Zhang
(74) *Attorney, Agent, or Firm* — Eric Grant Lee; Daniel Edward Agnew

(57) ABSTRACT

The present invention provides a system and method for assessing a synthetic peptide population including interrogating a population of peptide features in the presence of a receptor having an affinity for a binder sequence. The population of peptide features is synthesized over a plurality of synthesis periods and includes a plurality of control peptide features synthesized to have an amino acid sequence including the binder sequence. The control peptide features include a first feature synthesized beginning with a first one of the synthesis periods, and a second feature synthesized beginning after the first one of the synthesis periods such that synthesis of the second control peptide feature is delayed by at least one synthesis period. The method further includes detecting a signal output characteristic of an interaction of the receptor with the control peptide features, the signal output indicative of the fidelity of synthesis of the population of peptide features.

21 Claims, 7 Drawing Sheets

Specification includes a Sequence Listing.

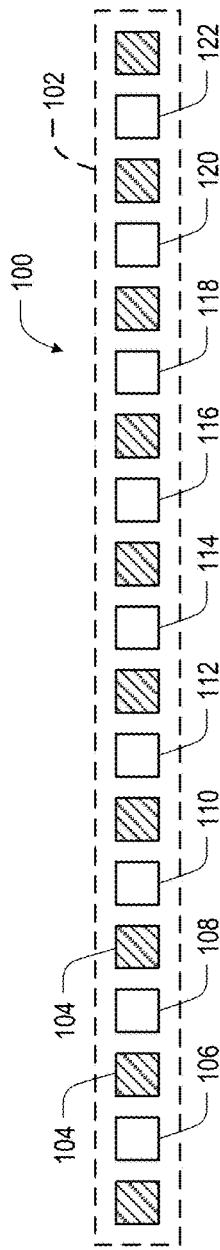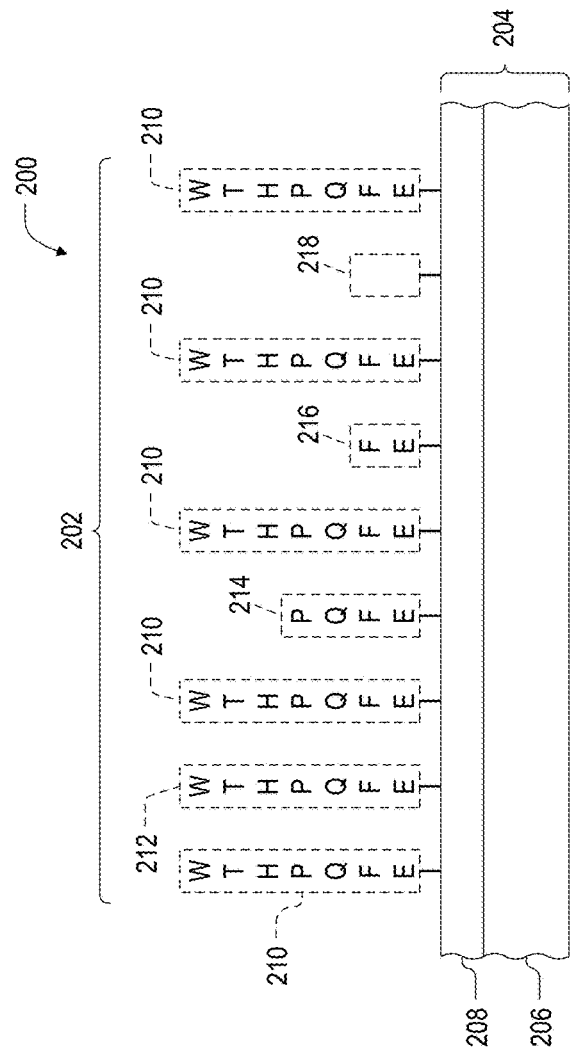

| Period | Cycle | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| 1 | A | R | N | D | C | E | Q | G | H | I | L | K | M | F | P | S | T | W | Y | V |
| 2 | A | R | N | D | C | [E] | [Q] | G | H | I | L | K | M | [F] | [P] | S | T | W | Y | V |
| 3 | A | R | N | D | C | E | Q | G | [H] | I | L | K | M | F | [P] | S | [T] | [W] | Y | V |
| 4 | A | R | N | D | C | E | Q | G | [H] | I | L | K | M | F | P | S | [T] | [W] | Y | V |
| 5 | A | R | N | D | C | E | Q | G | H | I | L | K | M | F | P | S | T | W | Y | V |
| 6 | A | R | N | D | C | (E) | (Q) | G | H | I | L | K | M | (F) | (P) | S | T | W | Y | V |
| 7 | A | R | N | D | C | (E) | Q | G | (H) | I | L | K | M | (F) | (P) | S | T | W | Y | V |
| 8 | A | R | N | D | C | E | Q | G | H | I | L | K | M | F | P | S | (T) | (W) | Y | V |
| 9 | A | R | N | D | C | E | Q | G | H | I | L | K | M | F | P | S | (T) | (W) | Y | V |

KEY: ▢ 1st subset  ▢ 2nd subset  ⚪ 6th subset  ◯ 7th subset

FIG. 3

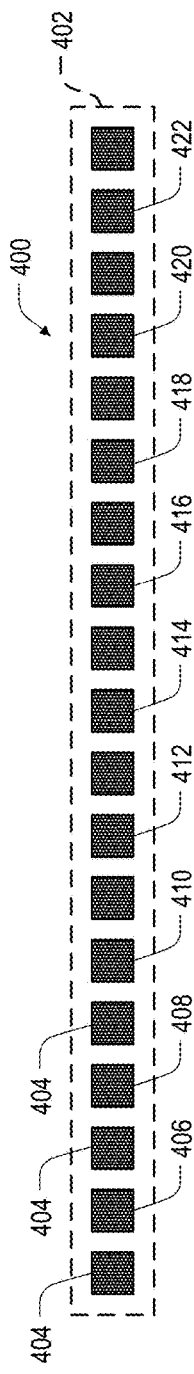
FIG. 8
FIG. 9
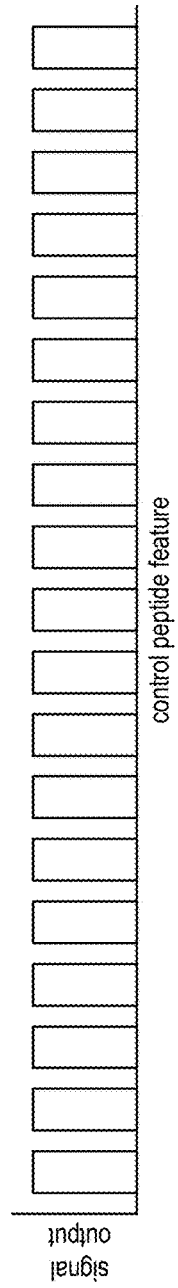
FIG. 10
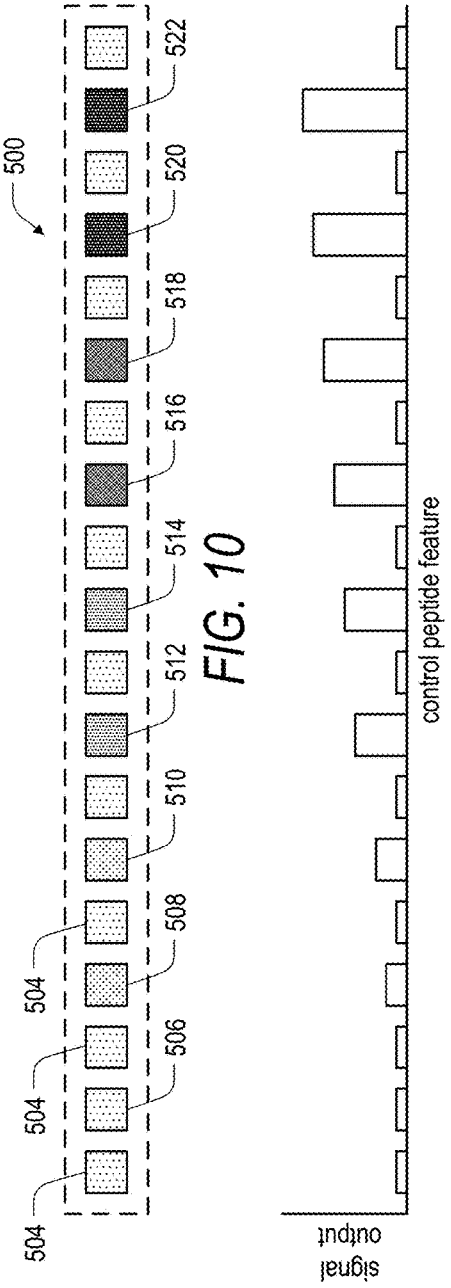
FIG. 11

SYSTEM AND METHOD FOR LONGITUDINAL ANALYSIS OF PEPTIDE SYNTHESIS

CROSS-REFERENCE TO RELATED APPLICATIONS

This application is based on, claims the benefit of, and incorporates herein by reference U.S. Provisional Patent Application Ser. No. 62/247,485 filed on 28 Oct. 2015 and entitled, "System and Method for Longitudinal Analysis of Peptide Synthesis."

STATEMENT REGARDING FEDERALLY SPONSORED RESEARCH

Not applicable.

SEQUENCE LISTING

The instant application contains a Sequence Listing which has been submitted electronically in ASCII format and is hereby incorporated by reference in its entirety. Said ASCII copy, created on Jul. 21, 2017, is named 33010-US1_SL.txt and is 1,321 bytes in size.

BACKGROUND OF THE INVENTION

The disclosure relates, in general, to evaluating peptide synthesis and, more particularly, to a system and method for identifying and implementing quality control oligopeptide sequences for assaying longitudinal peptide synthesis fidelity.

Peptides are biological polymers assembled, in part, through the formation of amide bonds between amino acid monomer units. In general, peptides may be distinguished from their protein counterparts based on factors such as size (e.g., number of monomer units or molecular weight), complexity (e.g., number of peptides, presence of coenzymes, cofactors, or other ligands), and the like. Experimental approaches for the identification of binding motifs, epitopes, mimotopes, disease markers, or the like may successfully employ peptides instead of larger or more complex proteins that may be more difficult to obtain or manipulate. As a result, the study of peptides and the capability to synthesize those peptides are of significant interest in the biological sciences and medicine.

Several methods exist for the synthesis of peptides including both in vivo and in vitro translation systems, as well as organic synthesis routes such as solid phase peptide synthesis. Solid phase peptide synthesis is a technique in which an initial amino acid is linked to a solid surface such as a bead, a microscope slide, or another like surface. Thereafter, subsequent amino acids are added in a step-wise manner to the initial amino acid to form a peptide chain. Because the peptide chain is attached to a solid surface, operations such as wash steps, side chain modifications, cyclization, or other treatment steps may be performed with the peptide chain maintained in a discrete location.

Recent advances in solid phase peptide synthesis have led to automated synthesis platforms for the parallel assembly of millions of unique peptide features in an array on a single surface (e.g., a ~75 mm×~25 mm microscope slide). The utility of such peptide arrays is, at least in part, dependent on the accuracy and fidelity with which the synthesis is carried out. For example, if the reagents used for synthesis are degraded, contaminated or improperly transported to the array surface during synthesis, a given peptide feature may have an altered, incomplete, or truncated peptide sequence. Other errors in peptide synthesis may also occur. However, it is generally impractical with currently available technologies to assay the quality of every individual feature on a routine basis due to both the number of features synthesized on a given array, and the associated material mass synthesized for each feature.

Accordingly, there is a need for improved processes and systems for the analysis of synthesis fidelity for peptide arrays as well as for peptide synthesis in general.

SUMMARY OF THE INVENTION

The present invention overcomes the aforementioned drawbacks by providing a system and method for analysis of peptide synthesis fidelity.

In accordance with one embodiment of the present disclosure, a method of assessing a synthetic peptide population includes interrogating a population of peptide features in the presence of a receptor having an affinity for a binder sequence. The population of peptide features is synthesized over a plurality of synthesis periods, and includes a plurality of control peptide features synthesized to have an amino acid sequence including the binder sequence. The plurality of control peptide features includes a first control peptide feature synthesized beginning with a first one of the plurality of synthesis periods, and a second control peptide feature synthesized beginning after the first one of the plurality of synthesis periods such that synthesis of the second control peptide feature is delayed by at least one synthesis period. The method further includes detecting a signal output characteristic of an interaction of the receptor with the plurality of control peptide features, the signal output indicative of the fidelity of synthesis of the population of peptide features.

In one aspect, each of the plurality of synthesis periods comprises a plurality of synthesis cycles, wherein each of the plurality of synthesis cycles corresponds to the addition of a selected amino acid.

In another aspect, the binder sequence is a streptavidin binder sequence, and the receptor is streptavidin.

In yet another aspect, the plurality of control peptides is synthesizable over a minimum number of synthesis periods, and at least a portion of the plurality of control peptides is synthesized over a number of synthesis periods greater than the minimum number of synthesis periods. Further, in some embodiments the minimum number of synthesis periods is at least two synthesis periods.

In a further aspect, the method includes contacting the population of peptide features in the presence of the receptor with a fluorescent probe capable of binding to the receptor. The signal output is a fluorescence intensity obtained through fluorophore excitation-emission, the fluorescence intensity reflecting at least one of an abundance of a portion of the receptor associated with the plurality of control peptide features and a binding affinity of the receptor to the plurality of control peptide features.

In one aspect, the population of peptide features is covalently bound to a solid surface in an array. In some embodiments, the peptide features are bound to the solid surface at a density of at least about 100,000 features per square centimeter.

In yet another aspect, the output signal of the receptor is known for each of the plurality of binder sequences.

In still another aspect, the population of peptide features is prepared using maskless array synthesis.

In still another aspect, the control peptide features are synthesized to have at least a first amino acid sequence including a first binder sequence and a second amino acid sequence including a second binder sequence different from the first binder sequence. The receptor has an affinity for each of the first binder sequence and the second binder sequence.

In accordance with another embodiment of the present disclosure, a method of assessing the fidelity of a synthetic peptide population includes synthesizing a population of peptide features on a solid surface over a plurality of sequential synthesis periods. The population of peptide features includes a plurality of sample peptide features and a plurality of control peptide features synthesized to have an amino acid sequence including a binder sequence. The control peptide features include a first control peptide feature synthesized beginning with a first one of the plurality of synthesis periods, and a second control peptide feature synthesized beginning after the first one of the plurality of synthesis periods such that synthesis of the second control peptide feature is delayed by at least one synthesis period. The method further includes contacting the population of peptide features on the solid surface with a receptor having an affinity for the binder sequence, and detecting an output characteristic of an interaction of the receptor with each of the control peptide features. The output is indicative of the longitudinal fidelity of synthesis of the population of peptide features.

In one aspect, each of the plurality of synthesis periods comprises a plurality of synthesis cycles, and each of the plurality of synthesis cycles corresponds to the addition of a selected amino acid.

In another aspect, the binder sequence is a streptavidin binder sequence, and the receptor is streptavidin.

In yet another aspect, the plurality of control peptides is synthesizable over a minimum number of synthesis periods, and wherein at least a portion of the plurality of control peptides is synthesized over a number of synthesis periods greater than the minimum number of synthesis periods.

In a further aspect, the method includes contacting the population of peptide features in the presence of the receptor with a fluorescent probe capable of binding to the receptor. The signal output is a fluorescence intensity obtained through fluorophore excitation-emission, the fluorescence intensity reflecting at least one of an abundance of a portion of the receptor associated with the plurality of control peptide features and a binding affinity of the receptor to the plurality of control peptide features.

In still another aspect, each of the sample peptide features has a defined sequence. In some embodiments, the peptide features are bound to the solid surface at a density of at least about 100,000 features per square centimeter.

In one aspect, the output signal of the receptor is known for each of the plurality of binder sequences.

In another aspect, the population of peptide features is prepared using maskless array synthesis.

In still another aspect, the control peptide features are synthesized to have at least a first amino acid sequence including a first binder sequence and a second amino acid sequence including a second binder sequence different from the first binder sequence. The receptor has an affinity for each of the first binder sequence and the second binder sequence.

In accordance with a further embodiment of the present disclosure, a synthetic peptide array includes an array substrate comprising a solid support having a reactive surface, and a population of peptide features immobilized on the reactive surface. The population of peptide features is synthesized over a plurality of sequential synthesis periods and includes a plurality of control peptide features synthesized to have an amino acid sequence including a binder sequence. The plurality of control peptide features includes a first control peptide feature synthesized beginning with a first one of the plurality of synthesis periods, and a second control peptide feature synthesized beginning after the first one of the plurality of synthesis periods such that synthesis of the second control peptide feature is delayed by at least one synthesis period. Detecting a signal output characteristic of an interaction of a receptor with each of the control peptide features is indicative of the fidelity of synthesis of the population of peptide features.

In one aspect, the binder sequence is a streptavidin binder sequence, and the receptor is streptavidin.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1 is a schematic illustration showing a partial plan view of a peptide array including a plurality of control peptide features according to the present disclosure.

FIG. 2 is a partial elevational view of a peptide array similar to the peptide array of FIG. 1 at an intermediate time point during synthesis of the control peptide features. FIG. 2 discloses SEQ ID NOS 1, 1, 1, 5, 1, 1 and 1, respectively, in order of appearance.

FIG. 3 is a table showing a design scheme for a first example peptide array synthesis scheme that includes nine sequential synthesis periods, where each period includes twenty cycles, with one cycle allocated for each one of the twenty canonical amino acids.

FIG. 8 is a schematic illustration showing a partial plan view of an embodiment of a peptide array including a plurality of uniformly synthesized control peptide features.

FIG. 9 is an example plot of signal output for each of the control peptide features in the peptide array of FIG. 7.

FIG. 10 is a schematic illustration showing a partial plan view of an embodiment of a peptide array including a plurality of synthesized control peptide features exhibiting longitudinal variability.

FIG. 11 is an example plot of signal output for each of the control peptide features in the peptide array of FIG. 9.

Like numbers will be used to describe like parts from figure to figure throughout the following detailed description.

DETAILED DESCRIPTION OF THE INVENTION

I. Overview

Figure 4:
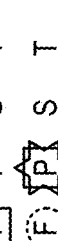
FIG. 4 is a table similar to FIG. 3 showing a design scheme for a second example peptide array synthesis scheme.

As also discussed above, in various situations it may be useful to provide quality control measures for assessing the fidelity of a plurality of synthetic peptides. Herein the terms fidelity and quality are used to mean the accuracy with which the desired sequence is replicated by synthesis. Accordingly, a synthesized peptide or peptide feature having high fidelity or quality has a peptide sequence that is substantially identical to a predefined or desired sequence with no insertions, substitutions, deletions, additions, or other like modifications. By contrast, a synthesized peptide or peptide feature having low fidelity or quality has a peptide sequence that includes one or more insertions, substitutions, deletions, additions, or other like modifications relative to the predefined or desired sequence. With respect to assessing the fidelity of a plurality of synthetic peptides, in one example, it may be useful to check for successful incorporation of each type of amino acid or other monomer unit used in the synthesis of one or more peptide features in a solid phase peptide synthesis operation. In another example, it may be useful to monitor the quality of reagents used for solid phase peptide synthesis along with any associated process equipment for delivery of the reagents. In yet another example, it may be useful to determine the overall quality of an array in a non-destructive manner, by analyzing only a small subset of peptides, the like, or combinations thereof. In still another example, it may be useful to monitor the quality of synthesis over time to ensure uniform synthesis quality from the beginning to the end of a particular peptide synthesis operation. Accordingly, many peptide synthesis schemes include various quality control sequences or analysis schemes to check for synthesis.

In one aspect, current quality control measures may pose several problems. For example, U.S. Pat. No. 6,955,915 to Fodor et al. describes a quality control method in which an initial binding profile may be measured for a fixed array design. Thereafter, binding profiles may be obtained for subsequent arrays of the same design for comparison with the initial binding profile. One challenge associated with this approach is that a new binding profile may need to be prepared for each unique array design. Further, a change in binding profiles between samples may not be informative as to the cause of the change. Yet other quality control methods may only indicate the general occurrence of an error, or in some limited cases (e.g., vertical tiling in oligonucleotide arrays), the occurrence of an error during a particular synthesis cycle. Moreover, it may be difficult to track changes in the quality or fidelity of synthesis across both synthesis cycles and synthesis periods (i.e., the longitudinal quality or fidelity). Ultimately, the aforementioned quality control methods do not enable tracking of either the particular cause of a synthesis error, or the longitudinal quality or fidelity of peptide synthesis. Further challenges may arise depending on the number of peptide features, the category of the solid surface (e.g., beads vs. arrays) upon which the synthesis is performed, the size or complexity of the synthesized peptide features, the duration of the peptide synthesis operation (e.g., number of synthesis steps, overall time, etc.), and the like.

These and other challenges may be overcome with a system and method for assessing longitudinal peptide synthesis fidelity according to the present disclosure. In one embodiment of the present disclosure, a control peptide feature having a particular binder sequence is synthesized multiple times over the course of synthesis of a broader population of peptide features. The quality of the control peptide features over time, as assessed by binding to a receptor having an affinity for the binder sequence, is used to determine the quality of the population of peptide features from a longitudinal or temporal perspective. Herein, the term "quality" refers to a measure of a characteristic or aspect of the component or feature in question. For example, the quality of a peptide feature can include the fidelity with which the sequence of the peptides was synthesized or reproduced, the fraction of peptides within a peptide feature that possess the correct sequence, or the like. In one aspect, the quality of a peptide (or peptide feature) may be determined by interrogating the interaction of the peptide with a receptor having a known affinity for a binder sequence included in the peptide. In another aspect, the term "drift" refers to the occurrence of longitudinal changes in synthesis quality or fidelity between synthesis cycles, synthesis periods, and combinations thereof.

In one example, synthesis of the population of peptide features is carried out over a number of synthesis periods, where each period is further divided into a plurality of synthesis cycles that correspond to the addition of one or more amino acids or other synthesis reagents. One or more control peptide features are synthesized beginning with the first period, and the quality of the one or more control peptide features are compared to subsequently synthesized control peptides where the initiation of synthesis was delayed by one or more synthesis cycles or synthesis periods. Initially, a control peptide is selected that can be completely synthesized over a minimum number of synthesis periods. In one example, a control peptide can be completely synthesized over a minimum of three (consecutive or non-consecutive) synthesis periods. For a synthesis run having a duration of twelve periods, initiation of synthesis of one or more of the selected control peptides may be delayed by up to (and including) nine periods, with the final set of control peptides synthesized over the final three periods (i.e., periods ten, eleven, and twelve). The synthesis run can then include control peptide features synthesized beginning at one or more of the first ten consecutive synthesis periods (of the twelve total synthesis periods) for longitudinal analysis of the quality of the broader population of peptide features.

In some embodiments, the quality of the synthesized control peptide features is determined by assaying reporter-labeled receptor binding to the control peptide features. In one example, receptor binding to control peptide features synthesized beginning with the initial synthesis period is compared to receptor binding to control peptide features synthesized beginning after the initial synthesis period. Differences in the observed binding of the receptor for the different control peptide features (either higher or lower reporter output signal) is indicative of a change in the longitudinal quality of the control peptide features (i.e., drift), and by extension, the quality of the overall population of peptide features. In one aspect, staggering synthesis of the control peptide features over the total number of synthesis periods enables longitudinal analysis of peptide synthesis.

With respect to timing of synthesis of the control peptides, the present disclosure provides for a variety of approaches. In some embodiments, each synthesis period includes a number of synthesis cycles or steps that are carried out in a fixed order. For example, synthesis of a population of peptide features using each of the twenty canonical amino acids can be performed over a number of synthesis periods having twenty cycles each, where each cycle corresponds to the addition of one of the twenty canonical amino acids. The order of the cycles dictates the minimum number of periods required to synthesize a given control peptide sequence. For an example control peptide feature having a sequence that can be synthesized over a minimum of three synthesis periods, a number of synthesis options exist. In a first approach, the control peptide feature can be completely synthesized over three consecutive (sequential) synthesis periods. In a second approach, synthesis of the control peptide feature can be distributed over three non-consecutive synthesis periods. In a third approach, synthesis of the control peptide feature can be distributed over greater than three (i.e., four or more) synthesis periods, which can be consecutive or non-consecutive. Notably, each of the aforementioned approaches can be used individually or in combination for synthesis of a plurality of control peptide features within a broader population of peptide features. Further, synthesis of control peptide features can be initiated beginning in a first or subsequent synthesis period such that the synthesis periods selected for synthesis of one control peptide feature partially overlap, completely overlap, or do not overlap at all with the synthesis periods selected for synthesis of another control peptide feature.

The use of reporter-labeled receptors having an affinity for binder sequences within the control peptides leverages measuring a signal output characteristic of an interaction of a receptor with a particular peptide sequence to detect an absolute or relative receptor affinity. The detected signal output can then be used to determine synthesis fidelity for a set of control peptides, and by extension, a broader population of peptides that includes the control peptides. In some embodiments, the aggregate data collected for a set of control peptides is indicative of a particular synthesis error. For example, interrogating a plurality of control peptides synthesized at various spatial locations across the array or at different times over the course of a synthesis operation may result in a measurable change in binding of the control peptide by a receptor having an affinity for the unique binder sequence. The resulting measurements can be analyzed to determine the likelihood of an occurrence of a substitution, deletion, or other synthesis error that occurred during array synthesis. Moreover, the design approach for how the control peptide features are synthesized as discussed above can be selected to elucidate whether or not a particular error or incident occurred during synthesis that affects the quality of the population of peptide features.

In summary, according to one embodiment of the present disclosure, successful synthesis of a population of peptides can be monitored by (i) characterizing a binder sequence-receptor pair where modification of the binder sequence results in a measurable change for a characteristic of an interaction (e.g., binding) of the receptor with the binder sequence, (ii) including in the population of peptides to be synthesized a control peptide having the characterized binder sequence, (iii) longitudinally staggering synthesis of the control peptides over the course of synthesis of the broader population of peptide features, and (iv) detecting the characteristic of the interaction following synthesis of the population of peptides to determine the overall quality of the temporally staggered control peptides, and by extension, the overall quality of the population of peptides, in general.

In one aspect, the present disclosure provides a method of assessing the longitudinal quality of a synthetic peptide population. For the purposes of the present disclosure, a synthetic peptide population includes any set of two or more peptides or peptide features (i.e., a grouping of two or more peptides having the same monomer sequence) prepared in a step-by-step chemical synthesis operation. For example, a synthetic peptide population may be prepared by solid phase peptide synthesis, where an initial amino acid is covalently bound to a solid surface either directly or via one or more linker molecules. Thereafter, subsequent amino acids may be added to the initial amino acid in directed or random fashion in order to prepare a population of peptide features arranged on a single surface such as a microscope slide, or distributed across a plurality of beads or other particle supports. One particular method for preparation of a population of synthetic peptides includes maskless array synthesis (MAS) technology (see, e.g., U.S. Pat. No. 8,658,572 to Albert et al.). However, other solid phase peptide synthesis methods, which are well known in the art, may be used for the formation of a synthetic peptide population according to the present disclosure.

For assessment of the synthetic peptide population, a method may include a first step of interrogating a population of peptide features in the presence of a receptor having an affinity for a plurality of binder sequences. A receptor includes any peptide, protein, antibody, small molecule, or other like structure that is capable of specifically binding a given peptide sequence or feature. In general, an aspect of the receptor should be detectable in order to determine whether the receptor is bound to a particular peptide or peptide feature. For example, the receptor itself may include a fluorophore that is detectable with a fluorescence microscope. Alternatively (or in addition), the receptor may be bound by a secondary molecule such as a fluorescent antibody. Further approaches will also fall within the scope of the present disclosure.

As described above the receptor is capable of binding to or otherwise interacting with a known binder sequence or affinity sequence. One example of a binder sequence is a defined amino acid sequence or motif. The defined amino acid sequence can represent at least a portion of a full length peptide within the synthetic peptide population. However, the binder sequence can itself be a full length peptide. For example, the eight amino acid peptide sequence Trp-Ser-His-Pro-Gln-Phe-Glu-Lys (i.e., WSHPQFEK (SEQ ID NO:3)) known as a "Strep-tag" exhibits intrinsic affinity towards an engineered form of the protein streptavidin. According to the present disclosure, a Strep-tag can be incorporated at either the N-terminus or the C-terminus of a given peptide or even incorporated at an intermediate point within a peptide. Thereafter, the peptide population including the peptides consisting of (or comprising) the Strep-tag binder sequence can be bound by the streptavidin receptor. Binding of streptavidin to the Strep-tag sequence can then be detected using various techniques. Further examples of binder sequences include the hexahistidine-tag (SEQ ID NO: 4) (His-tag). FLAG-tag, calmodulin-binding peptide, covalent yet dissociable peptide, heavy chain of protein C tag, and the like. Alternative (or additional) binder sequence-receptor pairs will also fall within the scope of the present disclosure.

With continued reference to binder sequences as disclosed herein, each binder sequence will have a particular or defined amino acid sequence. A binder sequence can include at least three amino acids. Example binder sequences disclosed here include between about five amino acids and about twelve amino acids. However, binder sequences having less than five or more than twelve amino acids can also be used. The positions of each amino acid in a particular binder sequence can be defined starting at either the N-terminus ([N]) or C-terminus ([C]). For example, the positions of the amino acids in the aforementioned Strep-tag binder sequence can be defined as [N]-Trp-Ser-His-Pro-Gln-Phe-Glu-Lys-[C] (SEQ ID NO:3). Accordingly, the position of the amino acid Histidine (His) is defined as the third amino acid from the N-terminus of the Strep-tag binder sequence. Notably, and as described above, the Strep-tag binder sequence can be flanked by one or more additional amino acids at either or both of the N-terminus and the C-terminus.

A population of peptide features as disclosed herein can further include one or more control peptides or control peptide features comprising multiple control peptides. A variety of control peptides having various functions or purposes can be included in a particular population of peptide features. However, at least a portion of these control peptides can be synthesized to have an amino acid sequence including a binder sequence. In one example, a control peptide amino acid sequence consists of the binder sequence. In another example, a control peptide amino acid sequence includes the binder sequence flanked by one or more additional amino acids at either or both of the N-terminus and the C-terminus. Control peptide features that are correctly synthesized and therefore include a binder sequence can be bound by a receptor having an affinity for the included binder sequence. On the other hand, control peptide features that are incorrectly synthesized may be bound with an altered affinity (or not bound at all) by the receptor. In the example case of the Strep-tag, a substitution or deletion including a selected one of the amino acids in the binder sequence (e.g., the amino acid His at the third position from the N-terminus of the Strep-tag binder sequence) may partially or completely disrupt the ability of the corresponding streptavidin receptor to bind the incorrectly synthesized control peptide that includes the Strep-tag binder sequence.

A method according to the present disclosure further includes detecting a signal output characteristic of an interaction of the receptor with a control peptide feature. A step of detecting a signal output can include any manner of monitoring or otherwise observing a measurable aspect of one or more peptides or peptide features within a population of peptides in the presence or absence of a receptor. Example signal outputs include an optical output (e.g., luminescence), an electrical output, a chemical output, the like, and combinations thereof. As a result, the step of detecting the signal output can include measuring, recording, or otherwise observing the signal output using any suitable instrument. Example instruments include optical and digital detection instruments such as fluorescence microscopes, digital cameras, or the like. In some embodiments, detecting a signal output further includes a perturbation such as excitation with light at one or more wavelengths, thermal manipulation, introduction of one or more chemical reagents, the like, and combinations thereof.

In some embodiments of the present system and method, the detected signal output is characteristic of an interaction of the receptor with a control peptide feature. As discussed above, depending on the actual sequence of the control peptide synthesized to incorporate the binder sequence, the receptor may have a variable interaction with the control peptide. For an example receptor-binder sequence pair, the receptor exhibits a strong affinity for a control peptide having the correct binder sequence; however, for a different control peptide having the binder sequence but possessing a synthesis error (e.g., an amino acid modification, substitution, or deletion within the binder sequence), the receptor exhibits a relatively weaker affinity for the flawed control peptide. The affinity (or interaction) of the receptor for each of the correct and flawed control peptides may be detected as a signal output characteristic of the interaction. Therefore, a corresponding signal output can be indicative of the fidelity of incorporation of the binder sequence into a control peptide or the quality of the control peptide, in general.

Returning again to the Strep-tag example, two distinct control peptides are synthesized to have the Strep-tag binder sequence. One of the control peptides (control peptide A) is accurately synthesized and possesses the full length Strep-tag binder sequence. The other of the control peptides (control peptide B) is synthesized incorrectly and as a result includes a deletion of the amino acid His at the third position from the N-terminus within the Strep-tag binder sequence. In the case that the His in question contributes the affinity of the streptavidin receptor to the Strep-tag binder sequence, the streptavidin receptor will have a higher affinity for control peptide A as compared with control peptide B. As a result, incubating each of control peptide A and control peptide B with a fluorescently-labelled streptavidin receptor leads to a relatively greater concentration of the labelled streptavidin receptor at the location of control peptide A and a relatively smaller concentration of the labelled streptavidin receptor at the location of control peptide B. The resulting differential fluorescent signal output from the locations of each of the control peptides is therefore characteristic of the interaction of the receptor with the control peptides. In particular, the signal output due to the streptavidin receptor affinity for the Strep-tag binder sequence is indicative of the fidelity of incorporation of the amino acid His into the control peptide. If each of the control peptides synthesized to have the Strep-tag binder sequence are interrogated and found to bind the streptavidin receptor more weakly than would be expected, it can be inferred that the greater population of peptides comprising the control peptides may also include synthesis errors related to the quality or delivery of synthesis reagents.

With continued reference to control peptides A and B from the aforementioned Strep-tag example, it will be appreciated that staggering the synthesis of the control peptides relative to one another may be useful for longitudinal analysis of the overall peptide synthesis operation. In one example, peptide A was synthesized beginning with the first period of a multi-period peptide synthesis operation, while peptide B was synthesized beginning at a later period (i.e., synthesis of peptide B was delayed relative to peptide A). Upon determining that there is differential binding of the control peptides A and B by the streptavidin receptor, it can be inferred that there was a change in the quality of peptide synthesis over the course of the overall peptide synthesis operation. In one aspect, an accurately synthesized control peptide A and an inaccurately synthesized control peptide B may be indicative of degradation of one or more peptide synthesis reagents over time, a malfunction or change to the process equipment used for peptide synthesis, or the like. In another aspect, if both control peptides A and B are found to include one or more synthesis errors (as determined by streptavidin receptor binding), then errors due to a temporal or longitudinal effect on peptide synthesis may be ruled out as a cause. It will be further appreciated that other patterns or observations based on temporally or longitudinally staggered control peptide synthesis can enable assessment and diagnosis of yet other peptide synthesis outcomes.

Notably, a synthetic peptide population can include a population of peptide features that is synthesized to include alternative building blocks such as non-natural amino acids, amino acid derivatives, or other monomer units altogether. In this case, one or more binder sequences can be prepared with each of the selected alternative building blocks. The binder sequences can then be used to interrogate the fidelity of incorporation of each of the alternative building blocks into a corresponding binder sequence. For example, it may be useful to synthesize a population of peptide features where at least some of the peptide features include the non-natural amino acid citrulline. In order to monitor whether citrulline was successfully incorporated into the population of peptide features, a binder sequence including at least one citrulline within the binder sequence that contributes to receptor binding can be identified. The binder sequence can be included as a control peptide feature within the overall population of peptide features. Further variations and alternative methodologies for assessing the fidelity of a synthetic peptide population according to the present disclosure will become apparent from the following detailed description.

II. Peptides

According to various embodiments of the instant disclosure, peptides (e.g., control peptides, peptide binder sequences) are disclosed. Each of the peptides includes two or more natural or non-natural amino acids as described herein. In examples described herein, a linear form of peptide is shown. However, one of skill in the art would immediately appreciate that the peptides can be converted to a cyclic form, e.g., by reacting the N-terminus with the C-terminus as disclosed in the U.S. Pat. Pub. No. 2015/0185216 to Albert et al. and filed on Dec. 19, 2014. The embodiments of the invention therefore include both cyclic peptides and linear peptides.

As used herein, the terms "peptide," "oligopeptide," and "peptide binder" refer to organic compounds composed of amino acids, which may be arranged in either a linear chain (joined together by peptide bonds between the carboxyl and amino groups of adjacent amino acid residues), in a cyclic form (cyclized using an internal site) or in a constrained form (e.g., "macrocycle" of head-to-tail cyclized form). The terms "peptide" or "oligopeptide" also refer to shorter polypeptides, i.e., organic compounds composed of less than 50 amino acid residues. A macrocycle (or constrained peptide), as used herein, is used in its customary meaning for describing a cyclic small molecule such as a peptide of about 500 Daltons to about 2,000 Daltons.

The term "natural amino acid" or "canonical amino acid" refers to one of the twenty amino acids typically found in proteins and used for protein biosynthesis as well as other amino acids which can be incorporated into proteins during translation (including pyrrolysine and selenocysteine). The twenty natural amino acids include the L-stereoisomers of histidine (His; H), alanine (Ala; A), valine (Val; V), glycine (Gly; G), leucine (Leu; L), isoleucine (Ile; I), aspartic acid (Asp; D), glutamic acid (Glu; E), serine (Ser; S), glutamine (Gln; Q), asparagine (Asn; N), threonine (Thr; T), arginine (Arg; R), proline (Pro; P), phenylalanine (Phe; F), tyrosine (Tyr; Y), tryptophan (Trp; W), cysteine (Cys; C), methionine (Met; M), and lysine (Lys; K). The term "all twenty amino acids" refers to the twenty natural amino acids listed above.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-stereoisomers of all twenty amino acids, the beta-amino-analogs of all twenty amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

According to embodiments of the instant disclosure, peptides are presented immobilized on a support surface (e.g., a microarray, a bead, or the like). In some embodiments, peptides selected for use as control peptides may optionally undergo one or more rounds of extension and maturation processes to yield the control peptides disclosed herein.

III. Microarrays

The control peptides disclosed herein can be generated using oligopeptide microarrays. As used herein, the term "microarray" refers to a two dimensional arrangement of features on the surface of a solid or semi-solid support. A single microarray or, in some cases, multiple microarrays (e.g., 3, 4, 5, or more microarrays) can be located on one solid support. For a solid support having fixed dimensions, the size of the microarrays depends on the number of microarrays on the solid support. That is, the higher the number of microarrays per solid support, the smaller the arrays have to be to fit on the solid support. The arrays can be designed in any shape, but preferably they are designed as squares or rectangles. The ready to use product is the oligopeptide microarray on the solid or semi-solid support (microarray slide).

The terms "peptide microarray" or "oligopeptide microarray," or "peptide chip," or "peptide epitope microarray" refer to a population or collection of peptides displayed on a microarray, i.e., a solid surface, for example a glass, carbon composite or plastic array, slide, or chip.

The term "feature" refers to a defined area on the surface of a microarray. The feature comprises biomolecules, such as peptides (i.e., a peptide feature), nucleic acids, carbohydrates, and the like. One feature can contain biomolecules with different properties, such as different sequences or orientations, as compared to other features. The size of a feature is determined by two factors: i) the number of features on an array, the higher the number of features on an array, the smaller is each single feature, ii) the number of individually addressable aluminum mirror elements which are used for the irradiation of one feature. The higher the number of mirror elements used for the irradiation of one feature, the bigger is each single feature. The number of features on an array may be limited by the number of mirror elements (pixels) present in the micromirror device. For example, the state of the art micromirror device from Texas Instruments, Inc. (Dallas, Tex.) currently contains 4.2 million mirror elements (pixels), thus the number of features within such exemplary microarray is therefore limited by this number. However, higher density arrays are possible with other micromirror devices.

The term "solid or semi-solid support" refers to any solid material, having a surface area to which organic molecules can be attached through bond formation or absorbed through electronic or static interactions such as covalent bonds or complex formation through a specific functional group. The support can be a combination of materials such as plastic on glass, carbon on glass, and the like. The functional surface can be simple organic molecules but can also comprise of co-polymers, dendrimers, molecular brushes, and the like.

The term "plastic" refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene). Most preferably, the plastic is a polyolefin with defined optical properties, like TOPAS® or ZEONOR/EX®.

The term "functional group" refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol, and nitril. Potentially reactive functional groups include, for example, amines, carboxylic acids, alcohols, double bonds, and the like. Preferred functional groups are potentially reactive functional groups of amino acids such as amino groups or carboxyl groups.

Various methods for the production of oligopeptide microarrays are known in the art. For example, spotting prefabricated peptides or in situ synthesis by spotting reagents (e.g., on membranes) exemplify known methods. Other known methods used for generating peptide arrays of higher density are the so-called photolithographic techniques, where the synthetic design of the desired biopolymers is controlled by suitable photolabile protecting groups (PLPG) releasing the linkage site for the respective next component (amino acid, oligonucleotide) upon exposure to electromagnetic radiation, such as light (Fodor et al., (1993) Nature 364:555-556; Fodor et al., (1991) Science 251:767-773). Two different photolithographic techniques are known in the state of the art. The first is a photolithographic mask, used to direct light to specific areas of the synthesis surface effecting localized deprotection of the PLPG. "Masked" methods include the synthesis of polymers utilizing a mount (e.g., a "mask") which engages a substrate and provides a reactor space between the substrate and the mount. Exemplary embodiments of such "masked" array synthesis are described in, for example, U.S. Pat. Nos. 5,143,854 and 5,445,934, the disclosures of which are hereby incorporated by reference. Potential drawbacks of this technique, however, include the need for a large number of masking steps resulting in a relatively low overall yield and high costs, e.g., the synthesis of a peptide of only six amino acids in length could require over 100 masks. The second photolithographic technique is the so-called maskless photolithography, where light is directed to specific areas of the synthesis surface effecting localized deprotection of the PLPG by digital projection technologies, such as micromirror devices (Singh-Gasson et al., Nature Biotechn. 17 (1999) 974-978). Such "maskless" array synthesis thus eliminates the need for time-consuming and expensive production of exposure masks. It should be understood that the embodiments of the systems and methods disclosed herein may comprise or utilize any of the various array synthesis techniques described above.

The use of PLPG (photolabile protecting groups), providing the basis for the photolithography based synthesis of oligopeptide microarrays, is well known in the art. Commonly used PLPG for photolithography based biopolymer synthesis are for example α-methyl-6-nitropiperonyl-oxycarbonyl (MeNPOC) (Pease et al., Proc. Natl. Acad. Sci. USA (1994) 91:5022-5026), 2-(2-nitrophenyl)-propoxycarbonyl (NPPOC) (Hasan et al. (1997) Tetrahedron 53: 4247-4264), nitroveratryloxycarbonyl (NVOC) (Fodor et al. (1991) Science 251:767-773) and 2-nitrobenzyloxycarbonyl (NBOC).

Amino acids have been introduced in photolithographic solid-phase peptide synthesis of oligopeptide microarrays, which were protected with NPPOC as a photolabile amino protecting group, wherein glass slides were used as a support (U.S. App. Pub. No. 20050101763). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement.

As understood by one of skill in the art, peptide microarrays comprise an assay principle whereby thousands (or in the case of the instant disclosure, millions) of peptides (in some embodiments presented in multiple copies) are linked or immobilized to the surface of a solid support (which in some embodiments comprises a glass, carbon composite or plastic chip or slide).

In some embodiments, a peptide microarray is exposed to a sample of interest such as a receptor, antibody, enzyme, peptide, oligonucleotide, or the like. The peptide microarray exposed to the sample of interest undergoes one or more washing steps, and then is subjected to a detection process. In some embodiments, the array is exposed to an antibody targeting the sample of interest (e.g. anti-IgG human/mouse or anti-phosphotyrosine or anti-myc). Usually, the secondary antibody is tagged by a fluorescent label that can be detected by a fluorescence scanner. Other detection methods are chemiluminescence, colorimetry, or autoradiography. In other embodiments, the sample of interest is biotinylated, and then detected by streptavidin conjugated to a fluorophore. In yet other embodiments, the protein of interest is tagged with specific tags, such as His-tag, FLAG-tag, Myc-tag, etc., and detected with a fluorophore-conjugated antibody specific for the tag.

After scanning the microarray slides, the scanner records a 20-bit, 16-bit or 8-bit numeric image in tagged image file format (*.tif). The tif-image enables interpretation and quantification of each fluorescent spot on the scanned microarray slide. This quantitative data is the basis for performing statistical analysis on measured binding events or peptide modifications on the microarray slide. For evaluation and interpretation of detected signals an allocation of the peptide spot (visible in the image) and the corresponding peptide sequence has to be performed.

A peptide microarray is a slide with peptides spotted onto it or assembled directly on the surface by in situ synthesis. Peptides are ideally covalently linked through a chemoselective bond leading to peptides with the same orientation for interaction profiling. Alternative procedures include unspecific covalent binding and adhesive immobilization.

According one specific embodiment of the instant disclosure, the specific peptide binders are identified using maskless array synthesis in the fabrication of the peptide binder probes on the substrate. According to such embodiments, the maskless array synthesis employed allows ultra-high density peptide synthesis of up to 2.9 million unique peptides, with each of the 2.9 million features/regions having up to $10^7$ reactive sites that could yield a full-length peptide. Smaller arrays can also be designed. For example, an array representing a comprehensive list of all possible 5-mer peptides using 19 natural amino acids excluding cysteine will have 2,476,099 peptides. In other examples, an array may include non-natural amino acids as well as natural amino acids. An array of 5-mer peptides by using all combinations of 18 natural amino acids excluding cysteine and methionine may also be used. Additionally, an array can exclude other amino acids or amino acid dimers. In some embodiments, an array may be designed to exclude any dimer or a longer repeat of the same amino acid, as well as any peptide containing HR, RH, HK, KH, RK, KR, HP, and PQ sequences to create a library of 1,360,732 unique peptides. Smaller arrays may have replicates of each peptide on the same array to increase the confidence of the conclusions drawn from array data.

In various embodiments, the peptide arrays described herein can have at least $1.6 \times 10^5$ peptides, or up to about $1.0 \times 10^8$ peptides or any number in-between, attached to the solid support of the peptide array. As described herein, a peptide array comprising a particular number of peptides can mean a single peptide array on a single solid support, or the peptides can be divided and attached to more than one solid support to obtain the number of peptides described herein.

Arrays synthesized in accordance with such embodiments can be designed for peptide binder discovery in the linear or cyclic form (as noted herein) and with and without modification such as N-methyl or other post-translational modifications. Arrays can also be designed for further extension of potential binders using a block-approach by performing iterative screens on the N-terminus and C-terminus of a potential hit (as is further described in detail herein). Once a hit of an ideal affinity has been discovered it can be further matured using a combination of maturation arrays (described further herein), that allow a combinatorial insertion, deletion and replacement analysis of various amino acids both natural and non-natural.

The peptide arrays of the instant disclosure are used to identify the specific binders or binder sequences of the invention as well as for maturation and extension of the binder sequences for use in the design and selection of control peptides.

IV. Design and Synthesis of Control Peptide Features

Turning now to FIG. 1, one embodiment of the present disclosure provides for a peptide array with a portion 100 of the peptide array including a plurality of control peptide features 102 for longitudinal analysis of the quality of a broader population of peptide features (not shown) including the control peptide features 102. While only a portion 100 of the peptide array is shown in FIG. 1, it will be appreciated that the peptide array can be designed comprising a population of hundreds, thousands, tens of thousands, hundreds of thousands and even millions of peptide features including or in addition to the control peptide features 102. In some embodiments, the population of peptide features on the portion 100 of the peptide array can be configured such that the peptide features collectively represent an entire protein, gene, chromosome, or even an entire genome of interest (e.g., a human proteome). Additionally, the peptide features can be configured according to specific criteria, whereby specific amino acids or motifs are excluded. Furthermore, the peptide features can be configured such that each of the peptide sequences comprises an identical length. For example, in some embodiments, the population of peptide features immobilized on an array substrate may all comprise 3-, 4-, 5-, 6-, 7-, 8-, 9-, 10-, 11-, or even 12-mers, or more. Notably, the sequences of the peptide features at specific locations on the array are known.

With reference to the portion 100 of the peptide array of FIG. 1, the control peptide features 102 can be repeated at a plurality of locations on the peptide array. The peptide array is illustrated to include nineteen control peptide features 102 within the portion 100. However, the peptide array can include a number of additional control peptide features 102. Alternative embodiments of peptide arrays according to the present disclosure can include any suitable number of control peptide features based on factors such as the size of the peptide array (e.g., number of total peptide features, number of features per unit area), the fidelity of the synthesis process, the number and type of reagents used (e.g., natural amino acids, non-natural amino acids, non-amino acid reagents), statistical requirements (e.g., number of replicates, statistical methods relied on), and the like. It will be appreciated that, while the figures illustrate the use of control peptide features synthesized to have the same sequence, embodiments of the present disclosure include peptide arrays having two or more control peptide sequences. Moreover, the two or more different control peptide sequences can be bound by the same receptor or different receptors.

In the embodiment illustrated in FIG. 1, each of the control peptide features 102 within the portion 100 are composed of a plurality of peptides that share the common peptide binder sequence [N]-WTHPQFE-[C] (i.e., WTHPQFE (SEQ ID NO:1)) that is selectively bound by the receptor streptavidin ([N] and [C] designate the N-terminus and C-terminus of the binder sequence, respectively). More particularly, each one of the control peptide features 102 is synthesized to be identical to each other one of the control peptide features 102 upon completion of synthesis of all the broader population of peptide features on the peptide array 100. Accordingly, if each of the nineteen control peptide features 102 in FIG. 1 is successfully synthesized without the occurrence of one or more substitutions, insertions, deletions, other like errors, or combinations thereof, then the control peptide features 102 will comprise a plurality of identical peptides, with each peptide having the peptide binder sequence WTHPQFE (SEQ ID NO:1).

In one aspect, while each of the control peptide features 102 may be identical following completion of synthesis, the timing of synthesis for each of the control peptide feature 102 can vary. As illustrated in FIG. 1, a first subset 104 of the control peptide features 102 (indicated as square features with diagonal hatching) are synthesized beginning with a first synthesis period of a twelve synthesis period process.

Each synthesis period is divided into a series of cycles where a single amino acid is exposed to the peptide array 100 per cycle for the step-wise assembly of the population of peptide features. For example, a first cycle can correspond to the addition of alanine, a second cycle to the addition of arginine, a third cycle to the addition of asparagine, and so forth. In the present example, each synthesis period is divided into 20 cycles, with each cycle corresponding to one of the twenty canonical amino acids as shown in Table 1. Over the course of N consecutive synthesis periods, a peptide array will be exposed to each amino acid (or other building block) N times, where N is a positive integer. Accordingly, in the present synthesis example having twelve periods, the peptide array in FIG. 1 is exposed to each amino acid a total of twelve times.

TABLE 1

| Cycle | Amino Acid (3-letter code) | Amino Acid (1-letter code) |
| --- | --- | --- |
| 1 | Ala | A |
| 2 | Arg | R |
| 3 | Asn | N |
| 4 | Asp | D |
| 5 | Cys | C |
| 6 | Gln | E |
| 7 | Glu | Q |
| 8 | Gly | G |
| 9 | His | H |
| 10 | Ile | I |
| 11 | Leu | L |
| 12 | Lys | K |
| 13 | Met | M |
| 14 | Phe | F |
| 15 | Pro | P |
| 16 | Ser | S |
| 17 | Thr | T |
| 18 | Trp | W |
| 19 | Tyr | Y |
| 20 | Val | V |

In the present example, the peptide binder sequence WTHPQFE (SEQ ID NO:1) can be synthesized from the C-terminus to the N-terminus over a minimum of three synthesis periods. With reference to Table 1, the amino acids Gln and Phe are synthesized in a first synthesis periods followed by the amino acids Glu and Pro in a second synthesis period and ending with the amino acids His, Thr, and Trp in a third synthesis period. For an example synthesis process having twelve synthesis periods, it is possible to delay initiation of synthesis of a control peptide having the peptide binder sequence WTHPQFE (SEQ ID NO:1) by up to and including nine periods, with synthesis beginning in the tenth period and taking place over synthesis periods ten, eleven, and twelve. In the design illustrated in FIG. 1, synthesis of at least one of the control peptide features 102 is initiated beginning with each one of the first ten (of the twelve total) synthesis periods. The first subset 104 of the control peptide feature 102 is synthesized beginning with the first one of the synthesis periods. Synthesis of the first subset 104 is then completed over the next two sequential synthesis periods (i.e., the second and third synthesis periods). A second subset 106 of the control peptide features 102 is synthesized beginning with the second synthesis period (i.e., after the first synthesis period). Synthesis of the second subset 106 is then completed over the next two sequential synthesis periods (i.e., the third and fourth synthesis periods). As a result, synthesis of the second subset 106 is delayed by one synthesis period relative to the first subset 104, and also overlaps with synthesis of the first subset 104 during the second and third synthesis periods.

The control peptide features 102 include additional subsets of control peptide features as illustrated in FIG. 1 such that synthesis of at least one of the control peptide features 102 begins in each of the first ten of the twelve total synthesis periods. In one aspect, the control peptide features 102 include a third subset 108, a fourth subset 110, a fifth subset 112, a sixth subset 114, and seventh subset 116, an eighth subset 118, a ninth subset 120, and a tenth subset 122. In comparison with the first subset 104 and second subset 106, the subsets 110-122 are each delayed by one synthesis period relative to the previous subset of the control peptide features 102. For example, initiation of synthesis of the third subset 108 begins with the third synthesis period, which is delayed by one synthesis period relative to initiation of synthesis of the second subset 106 (which begins with the second synthesis period). By extension, synthesis of the tenth subset 122, which is delayed by one synthesis period relative to the ninth subset 120, begins with the tenth period and is completed over the eleventh and twelfth synthesis periods.

Turning now to FIGS. 2 and 3, another example peptide array 200 includes a plurality of control peptide features 202 immobilized on an array substrate 204 that includes a solid support 206 having a reactive surface 208 (e.g., a reactive amine layer). Each of the peptide sequences of the control peptides features 202 is based on the streptavidin peptide binder sequence WTHPQFE (SEQ ID NO:1). Furthermore, while each of the control peptide features 202 is illustrated as a single peptide, it will be appreciated that each of the control peptide features 202 includes a plurality of co-localized peptides sharing the same amino acid sequence. Notably, there may be variations in the actual sequences of each of the peptides within a given peptide feature due to various limitations associated with synthesis process. However, for the purposes of illustration, the peptides within a peptide feature are assumed to comprise the same sequence.

The control peptide features 202 are synthesized over the course of nine synthesis periods, where each synthesis period is further divided into twenty synthesis cycles as shown in FIG. 3. The streptavidin peptide binder sequence WTHPQFE (SEQ ID NO:1), which is synthesized from the C-terminus to the N-terminus, can be synthesized over a minimum of three periods based on the order of the synthesis cycles for a synthesis period as shown in the table. According to one approach of the present disclosure, the control peptide features 202 are each built over three consecutive synthesis periods without skipping synthesis cycles or synthesis periods. For example, the amino acids Gln and Phe are synthesized in a first synthesis period followed by the amino acids Glu and Pro in a second synthesis period and ending with the amino acids His, Thr, and Trp in a third synthesis period, where each of the first, second, and third synthesis periods are uninterrupted consecutive synthesis periods. Using this uninterrupted synthesis approach, a first subset 210 of the control peptide features 202 is synthesized beginning with a first (initial) synthesis period, a second subset 212 of the control peptide features 202 is synthesized beginning with a second synthesis period, and a third subset 214 of the control peptide features 202 is synthesized beginning with a third synthesis period. Similarly, a fourth subset 216 of the control peptide features 202 is synthesized beginning with a fourth synthesis period, a fifth subset 218 of the control peptide features 202 is synthesized beginning with a fifth synthesis period, and so forth, where consecutively numbered synthesis periods are carried out in an uninterrupted consecutive manner.

Given that each of the control peptide features 202 is synthesized in an uninterrupted manner, it can be seen from FIG. 2 that only the first four synthesis periods have been completed (at least through cycle eighteen of synthesis period four; see Table 1) as the first subset 210 and the second subset 212 are illustrated as having the full length streptavidin binder sequence. The third subset 214 and fourth subset 216 are only partially complete, and synthesis of the fifth subset 218 has not yet begun, which indicates that the peptide synthesis operation is currently shown for a synthesis state between synthesis cycle nineteen of synthesis period four and synthesis cycle five of synthesis period five. In summary, the intermediate synthesis state in FIG. 2 illustrates that synthesis of the control peptide features 202 is staggered with a portion of the control peptide features 202 synthesized beginning with the initial or first synthesis period, and another portion of the control peptide features 202 synthesized beginning with subsequent synthesis periods (i.e., synthesis is delayed relative to the first synthesis period). As a result, the control peptide features 202 are continuously synthesized across each of the synthesis periods in a given synthesis operation.

With reference to synthesis scheme illustrated in FIG. 3, uninterrupted synthesis of the streptavidin peptide binder sequence WTHPQFE (SEQ ID NO:1) starting from the C-terminus is achieved over three synthesis periods given the illustrated order of synthesis cycles (see also Table 1). A first subset of control peptide features is synthesized over synthesis periods one, two, and three, with each of the relevant synthesis cycles used indicated by dashed squares. Following along with synthesis of the first subset of control peptide features, the amino acids Gln and Phe are synthesized in the first synthesis period at synthesis cycles six and fourteen, respectively. Next, the amino acids Glu and Pro are synthesized in the second synthesis period at synthesis cycles seven and fifteen, respectively. Finally, the amino acids His, Thr, and Trp are synthesized in the third synthesis period during corresponding synthesis cycles nine, seventeen, and eighteen. Notably, synthesis of other subsets of control peptide features is delayed relative to the first subset of control peptide features. In one aspect, a second subset of control peptide features is synthesized over synthesis periods two, three, and four as indicated by solid squares. In another aspect, a sixth subset of control peptide features is synthesized over synthesis periods six, seven, and eight as indicated by dashed circles. In yet another aspect, a seventh subset of control peptide features is synthesized over synthesis periods seven, eight, and nine as indicated by solid circles.

Whereas synthesis examples are explicitly shown for first, second, sixth, and seventh subsets of control peptide features, other subsets of control peptide features can be synthesized over the course of the synthesis operation illustrated in FIG. 3. For example, a third subset of control peptide features can be synthesized over synthesis periods three, four, and five such that synthesis of the third subset of control peptide features is delayed by one synthesis period relative to the second subset (solid squares). Moreover, the third subset of control peptide features is delayed by two synthesis periods relative to the first subset (dashed squares). Notably, control peptide features can be synthesized beginning with any of synthesis periods one through seven in order to complete synthesis of the control peptide features by the end of synthesis period nine (see, for example, the seventh subset of control peptide features indicated by solid circles).

According to another embodiment of the present disclosure, synthesis of one or more control peptide features is distributed across a greater number of synthesis periods or synthesis cycles than the minimum number required. For example, control peptide features can be synthesized across three or more consecutive or nonconsecutive synthesis periods. As described above and with reference to FIG. 3, synthesis of the streptavidin peptide binder sequence WTHPQFE (SEQ ID NO:1) may be achieved over a minimum of three synthesis periods. Turning to FIG. 4, the same streptavidin peptide binder sequence can be built in a number of alternative synthesis patterns over three or more consecutive or non-consecutive synthesis periods. In one example scheme, a first subset of control peptide features is synthesized over synthesis periods two, three, four, seven, and eight with each of the relevant synthesis cycles used indicated by solids stars. Following along with synthesis of the first subset of control peptide features, the amino acids Gln and Phe are synthesized starting in the second synthesis period (i.e., skipping the first synthesis period altogether) at synthesis cycles six and fourteen, respectively. Next, the amino acid Glu is synthesized in the third synthesis period at synthesis cycle seven. Then, the amino acid Pro is synthesized in the fourth synthesis period at synthesis cycle fifteen. After skipping synthesis periods five and six, the amino acid His is synthesized in the seventh synthesis period at synthesis cycle nine. Finally, the amino acids Thr and Trp are synthesized in the eighth synthesis period during corresponding synthesis cycles seventeen and eighteen.

With continued reference to FIG. 4, synthesis of other subsets of control peptide features is both delayed relative to, and overlapping with, the first subset of control peptide features. In one aspect, a second subset of control peptide features is synthesized in a continuous and uninterrupted manner over synthesis periods two, three, and four as indicated by solid squares. In another aspect, a third subset of control peptide features is synthesized in a semi-continuous manner over synthesis periods three, four, five, six, seven, eight, and nine as indicated by dashed circles. The term semi-continuous with respect to synthesis of the third subset indicates that the one or more possible synthesis cycles is skipped for a given synthesis period. For example, each of the amino acids Gln and Phe may be synthesized sequentially within the same synthesis period to completely synthesize the streptavidin binder sequence in the minimum possible number of synthesis periods and synthesis cycles. However, synthesis of the amino acids Gln and Phe is distributed across two different synthesis periods (i.e., synthesis periods three and four) for the third subset. Accordingly, although synthesis of the third subset is carried out over seven consecutive synthesis periods with no intermediate synthesis periods skipped or otherwise omitted between synthesis periods three and nine, synthesis of the third step is considered only semi-continuous as several possible synthesis cycles are skipped. More generally, a sequence or feature synthesized over a number of consecutive synthesis periods that is greater than the minimum possible number of synthesis periods is considered to have been synthesized semi-continuously.

Synthesis of the first subset, second subset, and third subset of control peptides illustrated in FIG. 4 overlaps in a number of ways. In one aspect, synthesis of the first subset overlaps with synthesis of second subset at synthesis cycle fifteen of synthesis period four. Synthesis of the first subset also overlaps with synthesis of third subset at synthesis cycle seventeen of synthesis period eight. In another aspect, synthesis of the second subset overlaps with synthesis of third subset at synthesis cycle six of synthesis period three. Accordingly, synthesis of each pair of the three subsets of control peptides in FIG. 4 overlaps for at least one particular combination of a synthesis period and synthesis cycle. Further synthesis overlaps can also be seen for different subsets of control peptides that share a particular synthesis period but not necessarily a synthesis cycle within the particular synthesis period. In one example, each of the first subset, second subset, and third subset of control peptides are partially synthesized during both the third and fourth synthesis periods. In another example, each of the second subset and third subset (but not the first subset) of control peptides are partially synthesized during the fifth synthesis period.

Notably, many variations and schemes are possible for the design of how and where synthesis of the various subsets of control peptide features overlaps. In some embodiments, it may be useful to have a design similar to that shown in FIG. 3 where a subset of control peptide features is initiated in each of the synthesis periods with each subset of control peptide features being further synthesized in a continuous and uninterrupted manner. In other embodiments, it may be useful to have a design similar to that shown in FIG. 4 where synthesis of at least a portion of the various subsets of control peptide features is carried out in a semi-continuous or discontinuous, interrupted manner. Each of the subsets of control peptide features can be synthesized using the same patterns of synthesis periods and synthesis cycles but delaying initiation of synthesis of each subset of control peptide features by one or more synthesis periods relative to another one or more of the control peptide features. Alternatively, each of the subsets of control peptide features can be synthesized using different synthesis patterns (e.g., as shown in FIG. 4).

Figure 5:
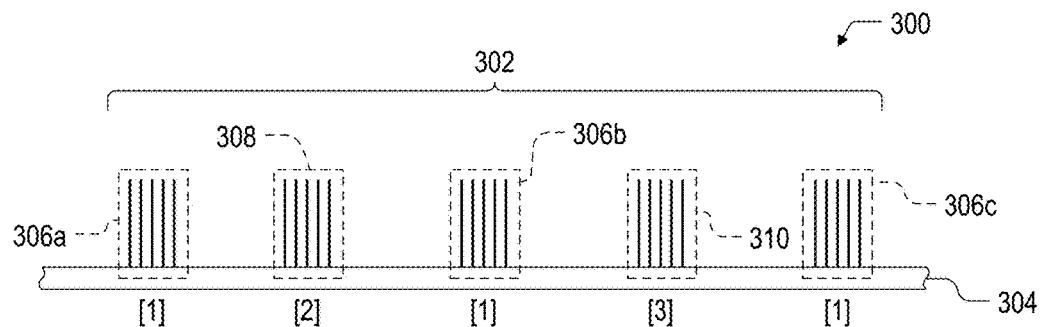
FIG. 5 is a schematic illustration of an embodiment of a peptide array including a population of peptide features for the interrogation and detection of control peptide features.
Figure 6:
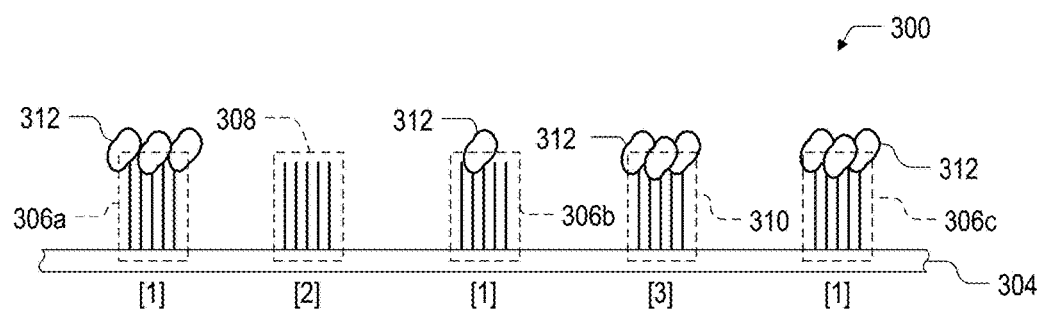
FIG. 6 is a schematic illustration of the peptide array of FIG. 5 following exposure of the control peptide features to a plurality of receptor molecules.
Figure 7:
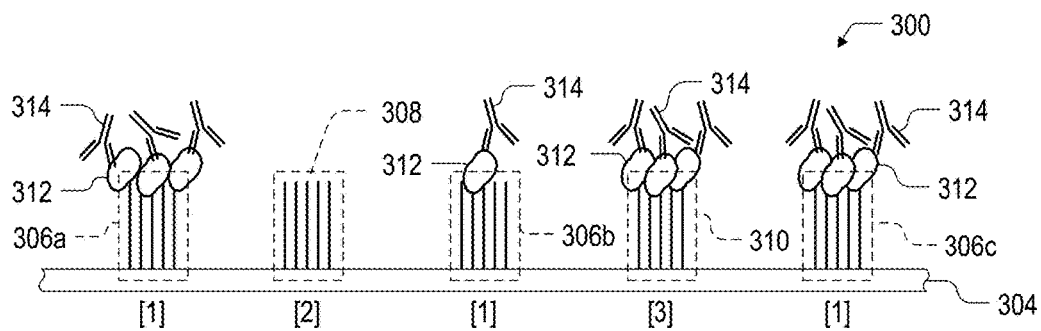
FIG. 7 is a schematic illustration of the peptide array of FIG. 6 following binding of a detectable tag to the receptor molecules.

In some embodiments, the design of synthesis for the control peptide features can be leveraged to generate an output that can be used to interpret whether or not one or more synthesis errors occurred during a given peptide synthesis operation. Turning to FIGS. 5-7, an example of longitudinal assessment of a synthetic peptide population can generally include interrogating a set of control peptide features synthesized over a plurality of synthesis periods in the presence of a receptor having an affinity for a binder sequence included in the control peptide features, and detecting a signal output characteristic of the interaction of the receptor with the control peptide features.

With reference to FIG. 5, a peptide array 300 includes a population of control peptide features 302 immobilized on an array substrate 304 and synthesized over the course of several synthesis periods. Each of the control peptide features 302 includes a plurality of colocalized peptides sharing the same amino acid sequence. It will be appreciated that in actuality, there may be variations in the actual sequences of each of the peptides within a given peptide feature due to various limitations associated with the synthesis process. However, for the purposes of illustration, the peptides within a peptide feature are assumed to comprise the same sequence. Depending on the synthesis method employed, a peptide feature may have a varying footprint or feature density. In one example, a peptide feature has a footprint of about 10 μm×10 μm square and includes up to about $10^7$ individual peptides. However, other footprints and feature densities are possible as will be recognized by a person of ordinary skill in the art. In the present example, the control peptide features 302 include a plurality of peptides that each have the amino acid sequence of the streptavidin binder sequence WTHPQFE (SEQ ID NO:1)).

The control peptide features 302 include a first subset 306 of control peptide features including a first feature 306a, a second feature 306b, and a third feature 306c. The control peptide features 302 further include a second subset 308 and a third subset 310 of control peptides features. Each of the control peptide features 302 are synthesized in a continuous, uninterrupted manner as described above with respect to FIGS. 2 and 3. Accordingly, synthesis of each of the control peptide features 302 is carried out over the course of three consecutive synthesis periods. For example, the first subset 306 is synthesized beginning with a first one of the plurality of synthesis periods as indicated by the '[1]' beneath each of the first feature 306a, the second feature 306b, and the third feature 306c. Synthesis of the first subset 306 is then completed over the course of the first, second, and third synthesis periods in a continuous and uninterrupted manner.

In another aspect, the second subset 308 and the third subset 310 are synthesized beginning after the first one of the plurality of synthesis periods such that synthesis of the second subset 308 and the third subset 310 of the control peptide features 302 is delayed by at least one synthesis period relative to the first subset 306. In the present example, the second subset 308 is synthesized beginning with the second one of the plurality of synthesis periods as indicated by the '[2]' beneath the illustrated feature of the second subset 308. The third subset 310 is synthesized beginning with the third one of the plurality of synthesis periods as indicated by the '[3]' beneath the illustrated feature of the third subset 310. As a result, synthesis of the first subset 306 overlaps with synthesis of the second subset 308 during synthesis periods two and three. Further, synthesis of the first subset 306 overlaps with synthesis of the third subset 310 during (only) synthesis period three. Notably, the peptide array 300 can include numerous peptide features beyond the number of features shown in the embodiment illustrated in FIGS. 5-7. Moreover, alternative or additional peptide features can also be included in a peptide array according to the present disclosure.

Once the peptide array 300 has been synthesized as illustrated in FIG. 5, a plurality of receptor molecules known to interact with the selected peptide binder sequences can be contacted to the peptide array 300 in order to interrogate the population of control peptide features 302 in the presence of the receptor molecules (FIG. 6). A number of receptor molecules 312 are shown as interacting with each of the feature 306a and the feature 306c of the first subset 306, as well as the illustrated feature of the third subset 310. Interaction of the receptor molecules 312 with the one or more of the control peptide features 302 can include binding, catalysis of (or participation in) a reaction including peptides within the corresponding ones of the control peptide features 302, digestion of the peptides within the control peptide features 302, the like, and combinations thereof. In the present example, the receptor molecules 312 represent streptavidin molecules used in the identification of the peptide binder sequence represented by the peptides in the control peptide features 302 (i.e., WTHPQFE (SEQ ID NO:1)). Accordingly, a strong degree of interaction between the peptides in the particular control peptide features 302 and the receptor molecules 312 would be anticipated as represented by the plurality of receptor molecules 312 associated with the various control peptide features 302. In one aspect, the interaction of the receptor molecules 312 with the control peptide features 302 on the peptide array 300 can be detected, for example, by labeling the receptor molecules 312 with a detectable tag 314 or other like reporter (FIG. 7). As shown in the illustrated embodiment, the detectable tag 314 is a labeled antibody that is specific for targeting the receptor molecules 312. However, other detection schemes are within the scope of the present disclosure.

Whereas a relatively greater number of receptor molecules 312 are associated with the feature 306a, the feature 306c, and the illustrated feature of the third subset 310 in FIG. 6, relatively fewer or no receptor molecules 312 are associated with any one of the feature 306b, or the illustrated feature of the second subset 308. In one aspect, an error in synthesis during one or more of the first, second, and third synthesis periods can affect the fidelity with which the streptavidin binder sequence is produced, thereby resulting in little to no interaction of the receptor molecules 312 with the indicated control peptide features 302. Similarly, the degree of interaction or the relative change in the extent of interaction of the receptor molecules 312 with any of the control peptide features 302 on the peptide array 300 can be interrogated. The results of the interrogation can be used to identify during which synthesis periods or synthesis cycles an error or other deviation in peptide synthesis occurred.

One possible result determined from interrogating the interaction of the receptor molecules 312 with the control peptide features 302 on the peptide array 300 can include the identification of an error associated with a particular synthesis cycle or synthesis period. For example, FIGS. 5-7 illustrate a hypothetical synthesis run in which an error occurred at synthesis cycle seven (addition of the amino acid Glu) during synthesis period three. The error resulted in the improper incorporation of the amino acid Glu into the second subset 308 of the control peptide features 302, leaving the corresponding features of the second subset 308 incapable of binding the receptor molecules 312. The detected signal output characteristic of the interaction of the receptor molecules 312 with the plurality of control peptide features 302 indicates that the second subset 308 of features was not bound by receptor molecules 312. By contrast, the detected signal output is indicative of binding of a relatively larger number of receptor molecules 312 to the first feature 306a, the third feature 306c, and the illustrated feature of the third subset 310. Based on this information, an inference can be made that an error occurred affecting only a particular synthesis cycle as opposed to an entire synthesis period. Moreover, the error affecting the particular synthesis cycle was likely confined to only one of the plurality of synthesis periods as opposed to each of the synthesis periods as the subset of the control peptide features 302 assembled in synthesis periods overlapping with the affected second subset 308 of features were not affected in the same way.

Based on the characterization of binding of the receptor molecules 312 in FIG. 7, determining which synthesis cycle (or cycles) were affected may require additional information or analysis. In one aspect, the signal output for features in the second subset 308 may be characteristic of a particular amino acid deletion. For example, the peptide array 300 may include one or more additional control peptide features (not shown) that represent each possible single amino acid deletion sequence corresponding to the streptavidin binder sequence represented by the control peptide features 302. The signal output for the second subset 308 can then be compared with the signal output for the additional control peptide features to determine whether a deletion may have occurred, and what the likely identity of the deleted amino acid was. If the outcome of the analysis indicates that a deletion occurred and the identity of the deleted amino acid can be elucidated, then the corresponding synthesis period and synthesis cycle during which the deletion error occurred can be determined. For example, following interrogation of the control peptide features 302, a binding profile for the illustrated feature of the second subset is determined to uniquely match with a binding profile for a control peptide binder with a known Glu deletion synthesized on the same peptide array 300. The amino acid Glu is incorporated during the third synthesis period for the second subset 308. Further, the first subset 306 and third subset 310 are found to have binding profiles that are indicative of synthesis of peptides having the correct, full-length binder sequence. Therefore, the determination can be made that only the third synthesis period was affected (out of at least synthesis periods two, three, and four), and further, that only the seventh synthesis cycle corresponding to the addition of Glu was affected during the third synthesis period.

Another possible result determined from interrogating the peptide array 300 of FIGS. 5-7 can include the identification of an error associated with a particular location on the array. For example, FIGS. 5-7 illustrate a hypothetical synthesis run in which an error occurred for the second feature 306b within the first subset 306. Each of the illustrated features of the first subset 306 were synthesized in parallel (i.e., in an identical manner using the same synthesis periods and synthesis cycles) with the only difference being the geographic location of synthesis on the surface of the peptide array 300. However, the second feature 306b exhibits relatively fewer interactions with the receptor molecules 312 as compared with either of the first feature 306a or the third feature 306c. Accordingly, an inference can be made that an error occurred during synthesis that affected at least the location of the second feature 306b. Based on the results of interrogating any additional feature adjacent to (or otherwise near) the second feature 306b, it may be possible to determine the quality or fidelity of peptide features near the second feature 306b. Yet other information related to the quality or fidelity of synthesis of the control peptide features 302, and by extension the broader population of peptide features can be determined based on the results of interrogating the control peptide features 302 as described herein. Moreover, whereas streptavidin-based receptor molecules and binder sequences are illustrated in the examples shown in the figures, alternative or additional receptor molecules and control peptide sequences can be used. Further methods and example peptide binder-receptors combinations are described by Albert et al. (U.S. Pat. App. No. 2015/0185216 to Albert et al. and U.S. Prov. Pat. App. Ser. No. 62/150,202 to Albert et al.).

V. Interrogation and Detection of Longitudinal Synthesis Fidelity

Notably, the examples described with respect to FIGS. 5-7 illustrate the identification of synthesis errors confined to particular locations, synthesis periods, synthesis cycles, or a combination thereof. However, embodiments of the present disclosure are also suited to the longitudinal analysis of peptide synthesis. Turning to FIGS. 8-11, hypothetical signal output profiles are illustrated for two different example peptide arrays. A portion of a first example peptide array 400 (FIGS. 8 and 9) includes a plurality of control peptide features 402 synthesized over a plurality of synthesis periods in a continuous uninterrupted pattern as described previously (e.g., with respect to FIG. 3). A first subset 404 of the control peptide features 402 were synthesized at every other location across the illustrated portion of the first example peptide array 400. Control peptide features alternately positioned with the first subset 404 include a second subset 406, a third subset 408, and a fourth through a tenth subset 410-422, respectively. The first subset 404 was synthesized beginning during the first of twelve sequential synthesis periods, with the beginning of synthesis for each of the following subsets (i.e., the second subset 406 through the tenth subset 422) being delayed by one synthesis period relative to the previously numbered subset. For example, the second subset 406 was synthesized beginning with the second synthesis period, the third subset 408 was synthesized beginning with the third synthesis period, and so forth, with the tenth subset 422 being synthesized beginning with the tenth synthesis period.

Following the completion of each of the twelve synthesis periods, each of the control peptide features 402 were interrogated in the presence of a receptor having an affinity for a binder sequence included in the control peptide features. The receptor molecules were labelled and detected to obtain a signal output indicative of the interaction between the control peptide features and the receptor molecules. The resulting signal was visualized both optically (FIG. 8) and graphically (FIG. 9) to determine the fidelity of synthesis of the control peptide features 402, and by extension, the broader population of peptide features (not shown) on the peptide array 400. With respect to the optical imaging approach, each of the control peptide features 402 are visually found to have substantially the same signal output as represented by the degree of shading of the boxes representing the control peptide features 402. It is noted that, with respect to FIGS. 8 and 10, a relatively darker shaded feature corresponds to a greater measured signal output, and therefore, a greater degree of interaction between the particular peptide feature and the receptor molecules. The measured signal output for each control peptide feature can also be plotted graphically, which generally corresponds to the signal output as a function of location on the surface of the peptide array 400. The graphical plot, as shown in FIG. 9 illustrates a trend similar to that observed in FIG. 8, where each of the control peptide features exhibits a uniform signal output. The signal output observed for the control peptide features 402 on the first example peptide array 400 is indicative of uniform synthesis between synthesis periods. Accordingly, it can be said that there is little to no 'drift' in the quality or fidelity of synthesis over the course of the twelve synthesis periods synthesis operation.

Turning to FIGS. 10 and 11, a portion of a second example peptide array 500 includes a plurality of control peptide features 502 synthesized over twelve synthesis periods in a continuous uninterrupted pattern as described for the peptide array 400. By way of comparison, a first subset 504 of the control peptide features 502 corresponds with the first subset 404, a second subset 506 corresponds with the second subset 406, and so forth, with the third through tenth subsets 508-522 corresponding to the third through tenth subsets 408-422. Following the completion of each of the twelve synthesis periods, each of the control peptide features 502 were interrogated as described above for the control peptide features 402 to obtain a signal output indicative of the interaction between the control peptide features 502 and the receptor molecules. The resulting signal was visualized both optically (FIG. 10) and graphically (FIG. 11) to determine the fidelity of synthesis of the control peptide features 502, and by extension, the broader population of peptide features (not shown) on the peptide array 500.

With respect to FIG. 10, each of the control peptide features 502 are observed to have an increasing signal output as a function of the synthesis period in which synthesis was initiated. For example, each of the illustrated features in the first subset 504 have the least shading (i.e., least signal output intensity), whereas the illustrated feature of tenth subset 522 has the darkest shading (i.e., greatest signal output intensity). Further, the shading increases with increasing subset number from the first subset 504 to the tenth subset 522. With reference to the graphical plot of measured signal output in FIG. 11, a trend similar to that observed in FIG. 10 further illustrates that each of the control peptide features 502 exhibits a variable signal output with the signal output increasing as a function of the synthesis period, with later synthesized features having relatively greater signal output intensity. The variable signal output observed for the control peptide features 502 on the second example peptide array 500 is indicative of non-uniform synthesis between synthesis periods. Accordingly, it can be said that there is drift in the quality or fidelity of synthesis over the course of the twelve synthesis periods that make up the synthesis operation.

In order to interpret the cause of the drift in the quality or fidelity of synthesis of a population of control peptide features, observation and analysis can be carried out for trends in the detected signal output characteristic of interaction of the receptor molecules with the plurality of control peptide features. For example, an observation of increasing signal output associated with control peptide features synthesized beginning with later synthesis periods in a synthesis operation (e.g., FIGS. 10 and 11) can indicate one or more possible errors or other adverse effects. In one aspect, the observed trend may be indicative of a blockage in one of the reagent supply lines that was slowly cleared over the course of the synthesis operation. The reduced supply of reagent (e.g., one or more amino acids) to the peptide array can result in incompletely or inaccurately synthesized control peptide features. In another aspect, the observed trend may indicate that synthesis reagents added in later synthesis periods were interacting with already synthesized control peptide features. In this case, amino acid reagents can react with side chains or other moieties associated with previously synthesized control peptide features, thereby reducing the ability of the those features to bind or otherwise interact with receptor molecules during downstream interrogation and detection steps.

In another example, an observation of decreasing signal output associated with control peptide features synthesized beginning with later synthesis periods in a synthesis operation can indicate yet other errors or other adverse effects. In one aspect, the observed trend may be indicative of a blockage in one of the reagent supply lines that developed over the course of the synthesis operation. As discussed above, the reduced supply of reagent (e.g., one or more amino acids) to the peptide array can result in incomplete or inaccurate synthesis for control peptide features synthesized during later synthesis periods. Still other errors and adverse effects are also possible. Accordingly, by first analyzing trends in signal output where there is drift present in the corresponding peptide synthesis operation, and then identifying the cause of the trend, a database of correlations can be prepared. Over time, the correlations can be recalled to quickly determine the cause (error or other adverse effect) associated with a particular trend in signal output data for a set of control peptide features on a peptide array. Moreover, by determining the cause of drift or other inconsistency in the signal output associated with control peptide features, an assessment can be made of the quality or fidelity of the broader population of peptide features (including the control peptide features) on the same peptide array.

Figure 12:
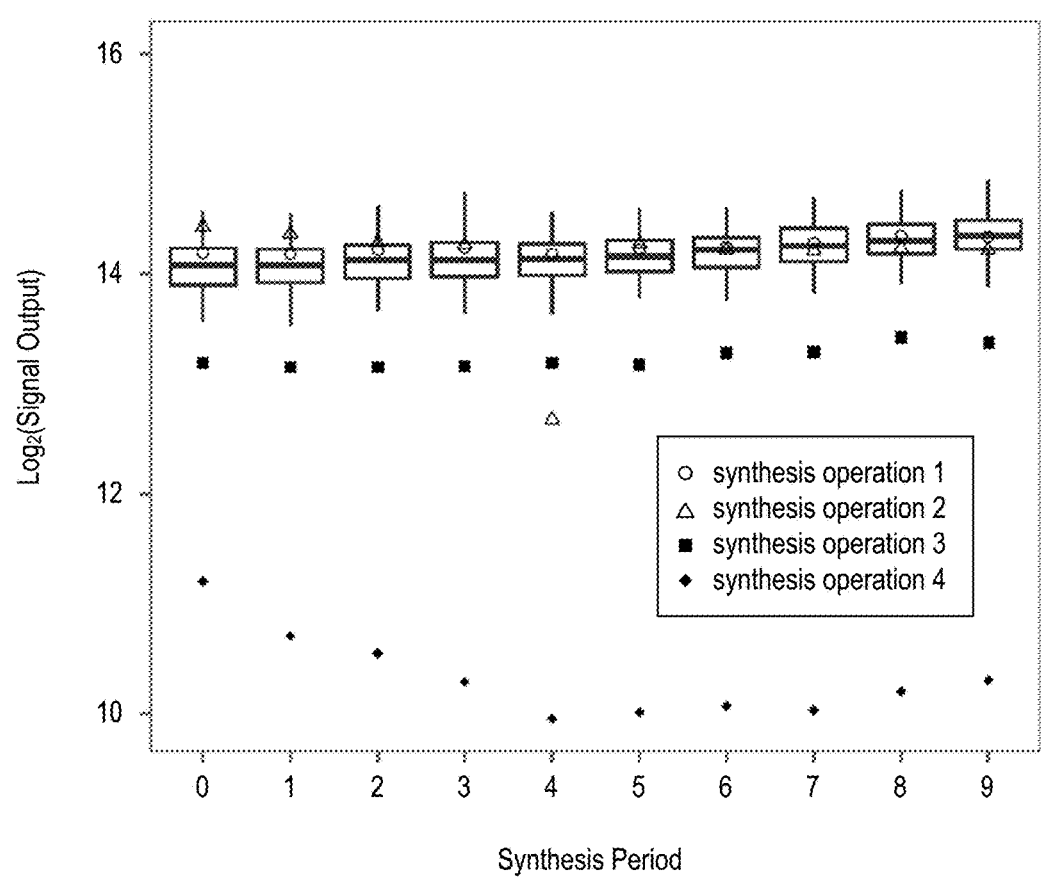
FIG. 12 is an example plot showing fluorescence signal output for a plurality of control peptide features from four separate synthesis operations as a function of synthesis period.

Whereas the hypothetical data presented in FIGS. 8-11 are for two example peptide arrays, actual signal output data following interrogation of a population of control peptide features can be presented in alternative or additional formats. With reference to FIG. 12, data was collected for a peptide array synthesis operation including twelve total synthesis periods. Control peptide features having the streptavidin binder sequence WTHPQFE (SEQ ID NO:1) were synthesized over three consecutive and uninterrupted synthesis periods (e.g., see FIG. 3) with control peptide features synthesized beginning with each of the first ten synthesis periods. Data included in the illustrated box plot chart corresponds to individual control peptide features within a population of control peptide features. The synthesis period in which synthesis began for each of the control peptide features is known (i.e., predetermined based on the design for synthesis of the peptide array). The signal output is measured for each of the control peptide features using one or more interrogation and detection techniques as described herein. Signal output is then plotted as a function of the synthesis period in which a given control peptide feature was initiated with statistical analysis performed on control peptide features synthesized in parallel (i.e., during the same synthesis periods and synthesis cycles).

As shown in FIG. 12, a standard box and whisker plot can be used to validate quality control data associated with control peptide features from a given synthesis operation against aggregate quality control data collected from a plurality of previous synthesis operations. In one example, data representing signal output as a function of receptor binding to control peptides synthesized beginning in a particular synthesis period can be combined from one or more synthesis operations to graphically depict groups of numerical data through their quartiles (defined by the upper and lower bounds of the boxes). Lines extending vertically from the boxes (whiskers) indicate variability outside the upper and lower quartiles. Individual data points for a given synthesis run can then be plotted alongside the combined (aggregate) data represented by the boxes and whiskers.

Data in FIG. 12 for a set of control peptides synthesized in a first synthesis operation (open circles) is generally aligned (i.e., overlaps) with the boxes, which generally represent a signal output range that is indicative of successful control peptide synthesis. Accordingly, the first synthesis operation unconditionally passes the quality control assessment. By contrast, data for a set of control peptides synthesized in a second synthesis operation (open triangles) is generally aligned with the boxes for each of the synthesis periods except for synthesis period four. As the low signal output measured for control peptides synthesized beginning in synthesis period four of the second synthesis operation is outside of the range indicated by both the box and whiskers in the corresponding period, the second synthesis operation fails the quality control assessment.

With continued reference to FIG. 12, each of the data points collected for both a third synthesis operation (filled squares) and a fourth synthesis operation (filled diamonds) falls outside of the range indicated by the boxes and whiskers. With respect to the data for the third synthesis operation, and taking into account the log-scale use for the vertical axis, although the total signal is somewhat low relative to the boxes and whiskers, the signal output is generally uniform at about $2^{13.4}$ units over the course of the synthesis operation. The data for the boxes and whiskers has a uniform signal output of about $2^{14.3}$ units over the course of the synthesis operation. In one aspect, the control peptides in the third synthesis operation may conditionally pass the quality control assessment as a signal output of $2^{13.4}$ units is still about 54% of $2^{14.3}$ units. However, it will be appreciated that other factors or analyses can be relied upon when determining whether the third synthesis operation will pass or fail the quality control assessment. With respect to the fourth set of control peptides, the signal output in the initial synthesis period (denoted synthesis period zero in FIG. 12) is about $2^{11.2}$ units. Thereafter the signal output steadily declines through synthesis period four, where the signal output drops to about $2^{9.9}$ units, which is about 5% of the signal output of the aggregate data (i.e., $2^{14.3}$ units). Given the decline in signal over the course of the several synthesis periods and the relatively low signal as a percentage of the aggregate data, the fourth synthesis operation fails the quality control assessment.

VI. Method of Assessing Longitudinal Fidelity

Figure 13:
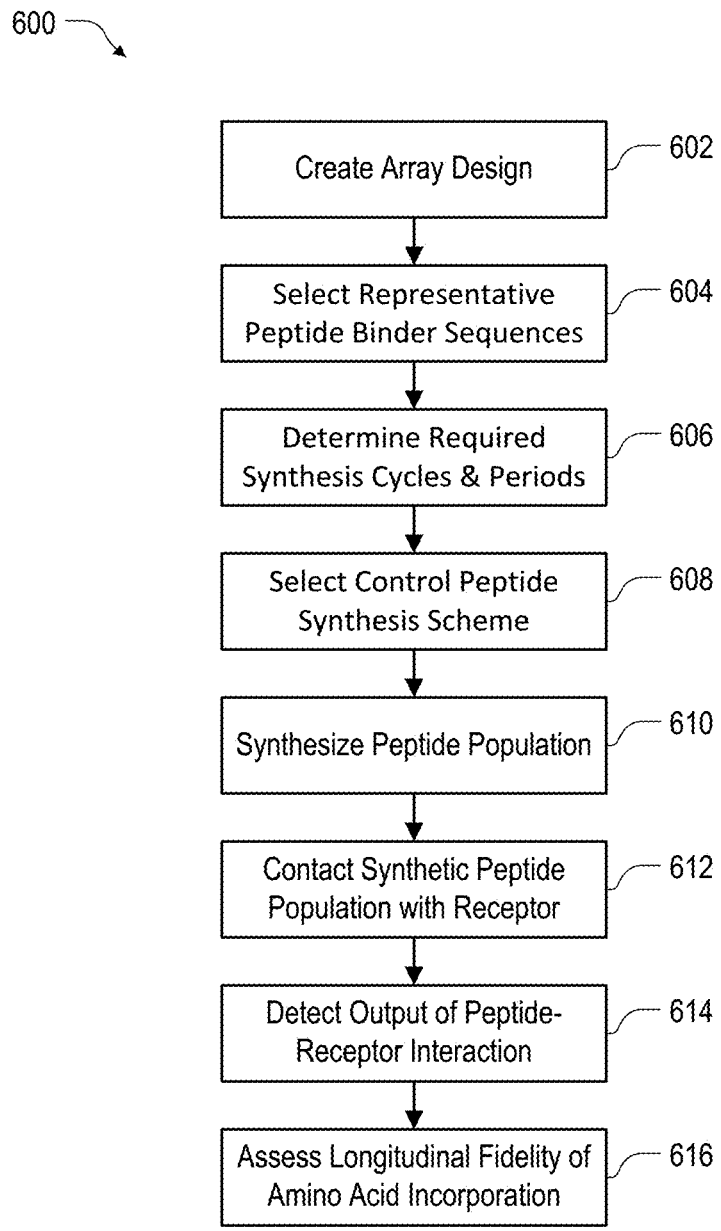
FIG. 13 is an example of a method for assessing the longitudinal fidelity of a synthetic peptide population according to the present disclosure.

Turning now to FIG. 13, a method 600 of assessing the fidelity of a synthetic peptide population includes a step 602 of creating an array design. The array design can include specifications for a particular number of peptide features including one or more natural amino acids, non-natural amino acids, or other like monomer units. The array design can further include specifications for the length of the one or more peptide features, the total number of monomer units required, and so forth. Based on the specifications of the array design, a step 604 of selecting representative peptide binders includes selection of at least one peptide binder sequence. In one aspect, the peptide binder sequence can be selected to include amino acids or other monomer units that are specified for use in the array design. However, a binder sequence can additionally or alternatively include monomer units that are not used for preparation of the peptide features specified in the step 602. As described above, one suitable peptide binder sequence includes the streptavidin binder sequence WTHPQFE (SEQ ID NO:1). However, other binder sequences can suitably be selected. One possible criterion for selecting a suitable binder sequence includes the existence of a detectable reported molecule that is capable of interacting with the binder sequence. Accordingly, it may be useful to select a binder sequence that is compatible with a known detection scheme.

In a next step 606, the number of synthesis cycles and synthesis periods required to synthesize each of the peptide features in the array design is determined. In one aspect, the number of synthesis cycles can depend on the number of unique monomers required for synthesis of the peptide features specified in the array design. For example, an array design including the twenty canonical amino acids may have at least twenty synthesis cycles with one synthesis cycle allocated for each of the twenty canonical amino acids. In another aspect, the number of synthesis periods required can depend on the number and order of synthesis cycles, the length of each of the peptide features, the complexity of the peptide features (e.g., the number of unique monomers per feature), the like, and combinations thereof.

Upon determining the number of synthesis cycles and synthesis periods in the step 606, the minimum number of synthesis periods can be determined for synthesizing the binder sequence selected in the step 604. For example, the streptavidin binder sequence WTHPQFE (SEQ ID NO:1) can be synthesized in a minimum of three synthesis periods using the synthesis scheme illustrated in FIG. 3. Given the number of synthesis cycle and synthesis periods, in a step 608 of the method 600, the control peptide synthesis scheme is selected. The synthesis scheme relates to how the one or more control peptide features will be synthesized over the course of the synthesis operation. For example, the control peptide features can be synthesized in a continuous uninterrupted manner with synthesis of a new control peptide feature initiated beginning in each of the first x-y synthesis periods, where x is the total number of synthesis periods in the synthesis operation and y is the minimum number of synthesis periods required to completely synthesize the selected control peptide feature. Notably, one example of the aforementioned continuous uninterrupted synthesis scheme is described herein with respect to at least FIG. 3. Other synthesis schemes can also be devised as described herein. In one aspect, design of a synthesis scheme can depend on factors such as the sequence of the control peptide features (e.g., number of monomer units, composition of monomer units), the number of synthesis periods, the number of synthesis cycles per synthesis period, and the like.

In a step 610 of the method 600, a synthetic peptide population is synthesized using any suitable method, including those methods described herein. The design of the synthetic peptide population includes the plurality of control peptide features where each of the control peptides includes one of the peptide binder sequences selected in the step 604. In one aspect, each of the control peptide features is synthesized to have an amino acid sequence including a selected one of the binder sequences. However, it is anticipated that one or more synthesis errors may occur that will result in control peptides having a sequence that differs from the selected peptide binder sequence. Errors that may occur during synthesis can include mechanical failures that impact delivery of the various reagents to the peptide array, degradation of one or more of the reagents, and the like. For example, each of the amino acids used for peptide synthesis is delivered from a separate reservoir. If one of the fluid connections to an amino acid reservoir fails, or if the amino acid reagent in the reservoir is degraded, then synthesis errors will be present for each peptide synthesized with the amino acid reagent in question. In certain situations, even though the error occurred, the peptide array can still be generated with the errors remaining initially undetected. As a result, the actual control peptide sequence can differ from the selected control peptide sequence.

In a next step 612 of the method 600, the synthetic peptide population is interrogated in the presence of a receptor having an affinity for the peptide binder sequences encoded by the control peptide features. In one aspect, the step 612 can include contacting the population of peptides with a plurality of receptor molecules (e.g., antibodies, peptides, proteins, enzymes, or the like). The receptor molecules can be unlabeled or labeled with a detectable tag such as a fluorescent marker. In another aspect, the step 612 can include labeling the receptor molecules with a detectable reporter molecule, such as a primary (and optionally a secondary) antibody, a dye, the like, or a combination thereof. Thereafter, in a step 614 of the method 600, an output of the peptide-receptor interaction is detected. The step 614 can include detecting the presence of the receptor using an optical technique (e.g., absorbance, luminescence, reflectance, etc.), a chemical technique (e.g., enzymatic assays), or another suitable method of detecting a signal output characteristic of an interaction of the receptor with the control peptides or control peptide features. In one aspect, the signal output is indicative of the fidelity of incorporation of a particular amino acid into a corresponding control peptide. Further, as the position of the particular amino acid in the control peptide sequence is known (i.e., the amino acid is at a defined position), it is further possible to assess whether the position of the amino acid is correct. Accordingly, based on the output detected in the step 614, a step 616 of the method 600 can include assessing the longitudinal fidelity of amino acid (or other like monomer) incorporation. That is, for a control peptide feature synthesized at a known location and over a known selection of synthesis periods and synthesis cycles, the detected interaction of a receptor in the presence of the control peptide feature is indicative of whether there is variation or drift in synthesis fidelity within or between synthesis cycles, within or between synthesis periods, or a combination thereof.

VII. Examples

In some embodiments, the present disclosure provides isolated artificial control peptides with specific affinity to streptavidin. In this embodiment, the disclosure includes peptides consisting of the sequence WTHPQFE (SEQ ID NO:1). The disclosure further includes peptides comprising alternative or additional binder sequences as described, for example, in U.S. patent application Ser. No. 15/233,543 to Bannen et al., filed on 10 Aug. 2016. Moreover, shorter or longer peptides (e.g., 5, 6, 7, 8, 9, and up to 20 amino acids) comprising sequences disclosed herein and elsewhere are also part of the invention.

As discussed herein, a control peptide including (or consisting of) WTHPQFE (SEQ ID NO:1) can be used to identify the longitudinal quality of a synthetic population of peptides including the control peptide. In one aspect any substitution, insertion, modification, or deletion at any position within the control peptide can result in a reduction or loss of signal corresponding to an interaction between the control peptide and the streptavidin receptor. Moreover, the reduction or loss of signal is distinguishable relative to the signal produced from the interaction between the streptavidin receptor and the control peptide in terms of both raw signal and signal relative to a control peptide having the substitution, insertion, modification, or deletion.

The peptide binders specific for streptavidin can be used as quality control peptides for any application that is compatible with the detection or capture of streptavidin, a fragment of streptavidin, or a streptavidin-biotin. However, other peptide binders can be similarly developed for a given receptor molecule other than streptavidin. Moreover, two or more different peptide binders (i.e., binders that differ in their amino acid sequence by at least one amino acid) that are each specific for streptavidin can be used simultaneously in a given peptide array design. Alternatively (or in addition), two or more different receptors can be used to detect one or more control peptide sequences.

In one example, a population of 2.88 million peptide features is synthesized on a 2.54 cm×7.62 cm array surface. Of the 2.88 million features synthesized, 228 of the features comprise control peptides features having the streptavidin peptide binder sequence for analysis of longitudinal synthesis fidelity. The control peptide features are grouped into blocks that are replicated at various locations across the array surface. In the present example case, each block comprises 19 control peptide features having the sequence WTHPQFE (SEQ ID NO:1). The control peptide features are arranges as shown in FIG. 1, such that control peptide features synthesized in an initial synthesis periods are alternated with control peptide features synthesized beginning in later synthesis periods. Each block of control peptide features is repeated 12 times across a single array for a total of 19×12 or 228 total control peptide features per array of 2.88 million peptide features. It will be appreciated, however, that a block of control peptides is not limited to the sequences described herein, and more than one control peptide sequence may be included in a given design for a peptide array.

Control peptide features are analyzed following the completion of a synthesis operation by array deprotection, streptavidin binding, and array scanning. Array deprotection to remove side-chain protecting groups is performed in 95% trifluoroacetic acid (TFA) and 0.5% Triisopropylsilane (TIPS) for 30 min. Arrays are then incubated twice successively in methanol for 30 seconds each, rinsed four times successively with reagent-grade water, and washed for one minute in TBST [1× Tris-buffered saline (TBS) and 0.05% Tween-20], and then washed twice successively in TBS for a duration of one minute for each wash. Streptavidin binding is performed by incubating arrays in a streptavidin bath [0.005 mg/ml Cy5-labeled streptavidin, 1% alkali-soluble casein, 0.5×TBS, and 0.05% Tween-20] for 1 hour at room temperature. Following streptavidin binding, arrays are washed twice in 1×TBS for a duration of one minutes per wash, with a final wash (30 seconds) in reagent-grade water. Streptavidin fluorescence signal is detected by scanning the array at 2 µm resolution and 15% gain with a 635 nm excitation wavelength using an MS200 microarray scanner.

Box and whisker plots for analysis of control peptide feature data are prepared in a two-part process. First, data is aggregated for a plurality of synthesis operations that were individually determined to pass a quality control assessment. Data was aggregated by calculating the median signal for peptides representing each synthesis period for each of the synthesis operations to determine a reference distribution of median signals for each synthesis period. Second, data for a given synthesis operation is collected and plotted alongside the aggregate data plotted as described above. For example, each of the data points for the synthesis operations in FIG. 12 represents the median signal output value of either twelve (12) control peptide features (synthesis periods one through nine) or one hundred and twenty (120) control peptide features (synthesis period zero). Notably, the initial synthesis period (i.e., synthesis period zero) includes 10-fold more features than the remaining synthesis periods due to the design of the blocks of control peptide features as described above and shown, for example, in FIG. 1.

In the above example, each of the control peptide features was synthesized to have the sequence WTHPQFE (SEQ ID NO:1). However, two or more different control peptide features including different binder sequences can be synthesized on a peptide array during the same synthesis operation. For example, it has been demonstrated that a peptide including the binder sequence FDEWL (SEQ ID NO:2) can be bound by streptavidin (see at least U.S. Patent Application Publication US2015/0185216 filed on 19 Dec. 2014 to Albert et al.). Accordingly, a peptide array synthesized according to the present disclosure can include a first population of control peptide features synthesized to have an amino acid sequence including the binder sequence WTH-PQFE (SEQ ID NO:1), and a second population of control peptide features synthesized to have an amino acid sequence including the binder sequence FDEWL (SEQ ID NO:2). In one aspect, the binder sequence FDEWL (SEQ ID NO:2) does not include the "HPQ" motif present in the binder sequence WTHPQFE (SEQ ID NO:1), and can therefore provide further information useful for analysis of control peptide feature data collected and visualized as described herein. For example, it may be determined that control peptides including the binder sequence FDEWL (SEQ ID NO:2) were successfully and accurately synthesized during one or more cycles or periods in which control peptides including the binder sequence WTHPQFE (SEQ ID NO:1) were incorrectly or improperly synthesized (i.e., as determined by interrogation of the peptides with streptavidin). In this case, it may be possible to determine that an error occurred with respect to one or more of the amino acids H, P or Q in control peptides including the binder sequence WTHPQFE (SEQ ID NO:1), as none of the amino acids H, P and Q are included in the binder sequence FDEWL (SEQ ID NO:2).

The schematic flow charts shown in the figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is presented in several varying embodiments in the following description with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

Each reference identified in the present application is herein incorporated by reference in its entirety.

What is claimed is:

1. A method of assessing a synthetic peptide population, the method comprising:
   interrogating a population of peptide features in the presence of a receptor having an affinity for a binder sequence, the population of peptide features synthesized over a plurality of synthesis periods, the population of peptide features including a plurality of control peptide features synthesized to have an amino acid sequence including the binder sequence, wherein the population of peptide features are covalently bound to a solid surface in an array, the plurality of control peptide features including:
      a first control peptide features synthesized beginning with a first one of the plurality of synthesis periods; and
      a second control peptide feature synthesized beginning after the first one of the plurality of synthesis periods such that synthesis of the second control peptide feature is delayed by at least one synthesis period; and
   detecting a signal output characteristic of an interaction of the receptor with the plurality of control peptide features, the signal output indicative of the fidelity of the synthesis of the population of the peptide features,
   wherein the binder sequence is a streptavidin binder sequence, wherein the streptavidin binder sequence comprises an amino acid sequence selected from a group consisting of SEQ ID NOs:1-3, and wherein the receptor is streptavidin.

2. The method of claim 1, wherein each of the plurality of synthesis periods comprises a plurality of synthesis cycles, wherein each of the plurality of synthesis cycles corresponds to the addition of a selected amino acid.

3. The method of claim 1, wherein the plurality of control peptides is synthesizable over a minimum number of synthesis periods, and wherein at least a portion of the plurality of control peptides is synthesized over a number of synthesis periods greater than the minimum number of synthesis periods.

4. The method of claim 3, wherein the minimum number of synthesis periods is at least two synthesis periods.

5. The method of claim 1, further comprising:
   contacting the population of peptide features in the presence of the receptor with a fluorescent probe capable of binding to the receptor, and
   wherein the signal output is a fluorescence intensity obtained through fluorophore excitation-emission, the fluorescence intensity reflecting at least one of an abundance of a portion of the receptor associated with the plurality of control peptide features and a binding affinity of the receptor to the plurality of control peptide features.

6. The method of claim 1, wherein the peptide features are bound to the solid surface at a density of at least 100,000 features per square centimeter.

7. The method of claim 1, wherein the output signal of the receptor is known for each of the binder sequences.

8. The method of claim 1, wherein the control peptide features are synthesized to have at least a first amino acid sequence including a first binder sequence and a second amino acid sequence including a second binder sequence different from the first binder sequence, the receptor having an affinity for each of the first binder sequence and the second binder sequence.

9. The method of claim 1, wherein the streptavidin binder sequence comprises an amino acid sequence consisting of SEQ ID NO:1.

10. The method of claim 1, wherein the streptavidin binder sequence comprises an amino acid sequence consisting of SEQ ID NO:2.

11. The method of claim 1, wherein the streptavidin binder sequence comprises an amino acid sequence consisting of SEQ ID NO:3.

12. A method of assessing the fidelity of a synthetic peptide population, the method comprising:
   synthesizing a population of peptide features on a solid surface over a plurality of sequential synthesis periods, the population of peptide features comprising a plurality of sample peptide features and a plurality of control peptide features synthesized to have an amino acid sequence including a binder sequence, the control peptide features including:
      a first control peptide feature synthesized beginning with a first one of the plurality of synthesis periods; and
      a second control peptide feature synthesized beginning after the first one of the plurality of synthesis periods such that synthesis of the second control peptide feature is delayed by at least one synthesis period;
   contacting the population of peptide features of the solid surface with a receptor having an affinity for the binder sequence; and
   detecting an output characteristic of an interaction of the receptor with each of the control peptide features,
   wherein the output is indicative of the longitudinal fidelity of synthesis of the population of peptide features,
   wherein the binder sequence is a streptavidin binder sequence, wherein the streptavidin binder sequence comprises an amino acid sequence selected from a group consisting of SEQ ID NOs:1-3, and wherein the receptor is streptavidin.

13. The method of claim 12, wherein each of the plurality of synthesis periods comprises a plurality of synthesis cycles, wherein each of the plurality of synthesis cycles corresponds to the addition of a selected amino acid.

14. The method of claim 12, wherein the plurality of control peptides is synthesizable over a minimum number of synthesis periods, and wherein at least a portion of the plurality of control peptides is synthesized over a number of synthesis periods greater than the minimum number of synthesis periods.

15. The method of claim 12, further comprising:
   contacting the population of peptide features in the presence of the receptor with a fluorescent probe capable of binding to the receptor,
   wherein the signal output is a fluorescence intensity obtained through fluorophore excitation-emission, the fluorescence intensity reflecting at least one of an abundance of a portion of the receptor associated with the plurality of control peptide features and a binding affinity of the receptor to the plurality of control peptide features.

16. The method of claim 12, wherein the peptide features are bound to the solid surface at a density of at least 100,000 features per square centimeter.

17. The method of claim 12, wherein the output single of the receptor is known for each of the binder sequences.

18. The method of claim 12, wherein the control peptide features are synthesized to have at least a first amino acid sequence including a first binder sequence and a second amino acid sequence including a second binder sequence different from the first binder sequence, the receptor having an affinity for each of the first binder sequence and the second binder sequence.

19. The method of claim 12, wherein the streptavidin binder sequence comprises an amino acid sequence consisting of SEQ ID NO:1.

20. The method of claim 12, wherein the streptavidin binder sequence comprises an amino acid sequence consisting of SEQ ID NO:2.

21. The method of claim 12, wherein the streptavidin binder sequence comprises an amino acid sequence consisting of SEQ ID NO:3.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Thr His Pro Gln Phe Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Asp Glu Trp Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ser His Pro Gln Phe Glu Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 4
<212> TYPE: PRT
<213> ORGANISM: Artificial Sequence
<220> FEATURE:
<221> NAME/KEY: source
<223> OTHER INFORMATION: Description of Artificial Sequence: Synthetic
      peptide

<400> SEQUENCE: 5

Pro Gln Phe Glu
1
```